United States Patent
Klee et al.

(10) Patent No.: US 6,369,164 B1
(45) Date of Patent: Apr. 9, 2002

(54) POLYMERIZABLE COMPOUNDS AND COMPOSITIONS

(75) Inventors: Joachim E. Klee, Radolfzell; Uwe Walz, Constance, both of (DE)

(73) Assignee: Dentsply G.m.b.H. (DE)

( * ) Notice: Subject to any disclaimer, the term of this patent is extended or adjusted under 35 U.S.C. 154(b) by 0 days.

(21) Appl. No.: 08/582,235

(22) Filed: Jan. 3, 1996

Related U.S. Application Data

(63) Continuation of application No. 08/359,217, filed on Dec. 19, 1994, now abandoned, which is a continuation-in-part of application No. 08/231,535, filed on Apr. 22, 1994, now abandoned, which is a continuation-in-part of application No. 08/217,998, filed on Mar. 25, 1994, now Pat. No. 5,624,976, which is a continuation-in-part of application No. 08/067,774, filed on May 26, 1993, now abandoned.

(51) Int. Cl.[7] .......................................... C08F 267/00
(52) U.S. Cl. ..................... 525/285; 525/287; 525/291; 525/301; 525/407; 525/531; 525/922; 523/105; 523/109; 526/277
(58) Field of Search ................................. 525/285, 287, 525/291, 301, 407, 531, 922; 523/109, 105

(56) References Cited

U.S. PATENT DOCUMENTS

| | | | |
|---|---|---|---|
| 150,262 A | 4/1874 | Slavin .......................... | 604/218 |
| 173,850 A | 2/1876 | Emde .......................... | 604/218 |
| 212,975 A | 4/1879 | Perkins et al. .............. | 604/218 |
| 543,829 A | 7/1895 | Gurnee ........................ | 604/218 |
| 3,066,112 A | 11/1962 | Bowen .......................... | 260/41 |
| D195,391 S | 6/1963 | Parkison ....................... | D81/1 |
| 3,150,801 A | 9/1964 | Hamilton .................... | 222/158 |
| 3,200,142 A | 8/1965 | Bowen .......................... | 260/286 |
| 3,256,226 A | 6/1966 | Fekete et al. .............. | 260/23.5 |
| 3,317,469 A | 5/1967 | Feichtinger et al. .......... | 260/47 |
| 3,327,016 A | 6/1967 | Lee .............................. | 260/830 |
| 3,327,017 A | 6/1967 | Huang et al. ................ | 260/844 |
| 3,466,259 A | 9/1969 | Jernigan ....................... | 260/37 |
| 3,503,128 A | 3/1970 | Boyd et al. ..................... | 32/15 |
| 3,539,533 A | 11/1970 | Lee, II et al. ................. | 260/17 |

(List continued on next page.)

FOREIGN PATENT DOCUMENTS

| CA | 563464 | 9/1958 |
|---|---|---|
| CA | 817442 | 7/1969 |
| CA | 878004 | 8/1971 |
| CA | 878006 | 8/1971 |
| CA | 1107751 | 8/1971 |
| CA | 966500 | 4/1975 |
| CA | 983491 | 2/1976 |
| CA | 987044 | 4/1976 |
| CA | 995667 | 8/1976 |
| CA | 1018294 | 9/1977 |
| CA | 1030979 | 5/1978 |
| CA | 1099848 | 4/1981 |
| CA | 1100990 | 5/1981 |
| CA | 1107293 | 8/1981 |
| CA | 1115289 | 12/1981 |

(List continued on next page.)

OTHER PUBLICATIONS

Klee et al, Synthesis and investigation of α, ω–methacryloyl poly (epoxide–carboxylic acid and αω–methacryloyl phenol) –macromonomers, Acta Polymer 44, 163–167 (1993).
Klee et al., Polym Bull. 27 (1992); 511–517.
J. Klee et al., Acta Polym. 42 (1991) 17–20.
Rot et al, Chemical Abstract, vol. 89, No. 18, Oct. 30, 1978, Columbus, Ohio, US; Abstract No. 148211c; page 71, column 2; *abstract* & Lakokras Mater. IKH. Primen., No. 4, pp. 50–52, 1978.
Dusek et al, Transesterification & Gelation of Polyhydroy Esters, Formed from Diepoxides & Dicarboxylic Acids, Amer. Chem. Societym 1984.
Hartel et al, Zur Synthese linearer Additionspolymere aus Diandiglycidether und Dicarbonsauren, (Nov. 1984).
Lal et al; Journal of Polymer Science: vol. XXIV, pp. 75–84 (1957) New Polymerization Catalysts for Methyl Methacrylate.
Beaunez et al: Journal of Polymer Science: Part A: Polymer Chemistry, vol. 32, pp. 1459–1469 (1994).
Antonucci et al; Journal of Dental Research 58 (9), pp. 1887–1899, Sep. 1979; New Initiator Systems for Dental Resins based on Ascorbic Acid.
Chemistry Abstract 115 (1991) 78952z and Chemistry Abstract 115 (1991) 78973g.

(List continued on next page.)

*Primary Examiner*—Margaret G. Moore
(74) *Attorney, Agent, or Firm*—Dale R. Lovercheck; James B. Bieber

(57) ABSTRACT

An esterified macromonomer within the scope of the general formula:

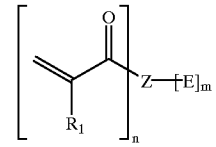

wherein Z is an organic moiety, $R_1$ is hydrogen or a substituted or unsubstituted alkyl having from 1 to 12 carbon atoms, oxyalkyl having from 1 to 12 carbon atoms, alkenyl having from 2 to 12 carbon atoms, cycloalkyl having from 5 to 12 carbon atoms, aryl having from 6 to 12 carbon atoms or aralkyl having from 7 to 12 carbon atoms, each E independently is a hydroxyl group, an organic ester moiety or an inorganic ester containing moiety and at least one E is an ester containing moiety, n and m each independently is an integer from 2 to 12. The esterified macromonomer is obtainable by esterification of at least a portion of the —OH groups of a macromonomer having at least one terminal double bond with at least one derivative of an inorganic or organic acid which introduces pendant groups exhibiting at least one acid moiety selected from the group of consisting of —COOH, —$PO_3H_2$, —$SO_3H$, —$BO_2H$ or salts thereof. The number of the acid moieties is chosen such that a polymer obtained by polymerizing those monomers has an adhesive strength to dentine of at least 2 MPa.

20 Claims, No Drawings

U.S. PATENT DOCUMENTS

| | | | | |
|---|---|---|---|---|
| 3,564,074 | A | 2/1971 | Swisher et al. | 260/837 |
| 3,586,527 | A | 6/1971 | Aronoff et al. | 117/93.31 |
| 3,595,969 | A | 7/1971 | Shepherd et al. | 260/28.5 |
| 3,634,542 | A | 1/1972 | Dowd et al. | 260/837 |
| 3,673,558 | A | 6/1972 | Toepel et al. | 260/29.2 |
| 3,709,866 | A | 1/1973 | Waller | 260/27 |
| 3,742,949 | A | 7/1973 | Hill | 128/218 |
| 3,754,054 | A | 8/1973 | Khnura et al. | 260/860 |
| 3,769,336 | A | 10/1973 | Lee, Jr. et al. | 260/486 |
| 3,815,239 | A | 6/1974 | Lee, Jr. et al. | 32/15 |
| 3,835,090 | A | 9/1974 | Gander et al. | 260/42.15 |
| 3,845,009 | A | 10/1974 | Gander | 260/42.15 |
| 3,853,962 | A | 12/1974 | Gander | 260/486 |
| 3,882,187 | A | 5/1975 | Takiyama et al. | 260/835 |
| 3,889,385 | A | 6/1975 | Dougherty | 32/12 |
| 3,926,906 | A | 12/1975 | Lee, II et al. | 260/42.53 |
| 3,971,765 | A | 7/1976 | Green et al. | 260/78 |
| 3,973,972 | A | 8/1976 | Muller | 106/39.7 |
| 3,980,483 | A | 9/1976 | Nishikubo et al. | 96/115 |
| 4,002,669 | A | 1/1977 | Gross et al. | 260/486 |
| 4,051,195 | A | 9/1977 | McWhorter | 260/837 |
| 4,081,492 | A | 3/1978 | Traenchner et al. | 260/837 |
| 4,097,569 | A | 6/1978 | Waters | 264/255 |
| 4,097,994 | A * | 7/1978 | Reaville et al. | 525/922 |
| 4,098,735 | A | 7/1978 | Tobias | 260/18 |
| 4,100,045 | A | 7/1978 | Bogan et al. | 204/159.16 |
| 4,135,868 | A | 1/1979 | Schainholz | 422/310 |
| 4,141,865 | A | 2/1979 | Bogan | 260/18 |
| 4,150,012 | A | 4/1979 | Joos | 260/42.15 |
| 4,177,563 | A | 12/1979 | Schmitz-Josten et al. | 433/228 |
| 4,182,035 | A | 1/1980 | Yamauchi et al. | 433/228 |
| 4,182,833 | A | 1/1980 | Hicks | 528/120 |
| 4,197,390 | A | 4/1980 | Jackson | 528/115 |
| 4,220,582 | A | 9/1980 | Orlowski et al. | 260/42.28 |
| 4,229,376 | A | 10/1980 | Rogier | 260/563 P |
| 4,253,830 | A | 3/1981 | Kazen et al. | 433/77 |
| 4,255,468 | A | 3/1981 | Olson | 427/137 |
| 4,256,457 | A | 3/1981 | Behring | 433/77 |
| 4,284,742 | A | 8/1981 | Bowerman, Jr. et al. | 525/329 |
| 4,293,074 | A | 10/1981 | Dunsky | 206/572 |
| 4,296,004 | A | 10/1981 | Rogier | 260/18 EP |
| 4,308,085 | A | 12/1981 | Horhold et al. | 156/330 |
| 4,362,889 | A | 12/1982 | Bowen | 560/221 |
| 4,368,889 | A | 1/1983 | Reker, Jr. | 273/243 |
| 4,383,826 | A | 5/1983 | Butler et al. | 433/228 |
| 4,383,879 | A | 5/1983 | Le Du et al. | 156/307 |
| 4,384,853 | A | 5/1983 | Welsh | 433/90 |
| 4,391,590 | A | 7/1983 | Dougherty | 433/90 |
| 4,405,766 | A | 9/1983 | Bertram et al. | 525/507 |
| 4,406,625 | A | 9/1983 | Orlowski et al. | 433/228 |
| 4,413,105 | A | 11/1983 | Koenig | 525/482 |
| 4,431,421 | A | 2/1984 | Kawahara et al. | 433/228 |
| 4,446,246 | A | 5/1984 | McGinniss | 502/155 |
| 4,467,079 | A | 8/1984 | Hechenberger et al. | 526/90 |
| 4,514,342 | A | 4/1985 | Billington et al. | 260/952 |
| 4,515,634 | A | 5/1985 | Wu et al. | 106/35 |
| 4,524,161 | A | 6/1985 | Feuerhahn | 523/414 |
| 4,541,992 | A | 9/1985 | Jerge et al. | 422/300 |
| 4,547,531 | A | 10/1985 | Waknine | 523/116 |
| 4,548,689 | A | 10/1985 | Sakashita et al. | 204/159.23 |
| 4,557,848 | A | 12/1985 | Sung et al. | 252/51.2 |
| 4,569,662 | A | 2/1986 | Dragan | 433/89 |
| 4,579,904 | A | 4/1986 | Orlowski et al. | 524/554 |
| 4,595,734 | A | 6/1986 | O'Hearn | 525/524 |
| 4,643,303 | A | 2/1987 | Arp et al. | 206/370 |
| 4,714,571 | A | 12/1987 | Schornick et al. | 528/103 |
| 4,714,751 | A | 12/1987 | Schornick et al. | 528/103 |
| 4,758,643 | A | 7/1988 | Tannaka et al. | 526/279 |
| 4,767,326 | A | 8/1988 | Bennett et al. | 433/90 |
| 4,774,063 | A | 9/1988 | Runnells | 422/297 |
| 4,781,921 | A | 11/1988 | Smith et al. | 424/81 |
| 4,789,620 | A * | 12/1988 | Sasaki et al. | 430/280 |
| 4,806,381 | A * | 2/1989 | Engelbercht et al. | 525/285 |
| 4,816,495 | A * | 3/1989 | Blackwell et al. | 522/14 |
| 4,816,528 | A | 3/1989 | Dervan et al. | 525/438 |
| 4,854,475 | A | 8/1989 | Riihimaki et al. | 220/337 |
| 4,863,993 | A | 9/1989 | Montgomery | 524/854 |
| 4,866,146 | A | 9/1989 | Janda et al. | 526/213 |
| 4,872,936 | A | 10/1989 | Engelbrecht | 156/307.3 |
| 4,874,799 | A | 10/1989 | Hung et al. | 522/96 |
| 4,883,899 | A | 11/1989 | Muramoto et al. | 560/14 |
| 4,918,136 | A | 4/1990 | Kawaguchi et al. | 524/751 |
| 4,931,096 | A | 6/1990 | Fujisawa et al. | 106/35 |
| 4,936,775 | A | 6/1990 | Bennett | 433/220 |
| 4,950,697 | A | 8/1990 | Chang et al. | 523/116 |
| 4,959,199 | A | 9/1990 | Brewer | 422/300 |
| 4,963,093 | A | 10/1990 | Dragan | 433/90 |
| 4,964,911 | A | 10/1990 | Ibsen et al. | 106/35 |
| 4,969,816 | A | 11/1990 | Drumm | 433/90 |
| 4,985,198 | A | 1/1991 | Hirasawa et al. | 560/130 |
| 4,985,516 | A | 1/1991 | Sakashita et al. | 526/196 |
| D315,956 | S | 4/1991 | Dragan | D24/14 |
| 5,006,066 | A | 4/1991 | Rouse | 433/77 |
| 5,052,927 | A | 10/1991 | Discko, Jr. | 433/90 |
| 5,083,921 | A | 1/1992 | Dragan | 433/90 |
| 5,100,320 | A | 3/1992 | Martin et al. | 433/90 |
| 5,106,301 | A | 4/1992 | Miyahara et al. | 433/214 |
| 5,108,287 | A | 4/1992 | Yee et al. | 433/77 |
| 5,122,057 | A | 6/1992 | Discko, Jr. | 433/90 |
| 5,129,825 | A | 7/1992 | Discko, Jr. | 433/90 |
| 5,137,990 | A | 8/1992 | Corley | 525/530 |
| 5,151,479 | A | 9/1992 | Mukai et al. | 526/277 |
| 5,165,890 | A | 11/1992 | Discko, Jr. | 433/90 |
| 5,166,117 | A | 11/1992 | Imai et al. | 502/169 |
| 5,172,810 | A | 12/1992 | Brewer | 206/369 |
| 5,173,273 | A | 12/1992 | Brewer | 422/300 |
| 5,189,077 | A | 2/1993 | Kerby | 523/116 |
| 5,204,398 | A | 4/1993 | Cohen et al. | 524/403 |
| 5,210,157 | A | 5/1993 | Schutyser et al. | 525/502 |
| 5,215,726 | A | 6/1993 | Kudla et al. | 422/297 |
| 5,217,372 | A | 6/1993 | Truocchio | 433/215 |
| 5,235,008 | A * | 8/1993 | Herner Jr. et al. | 525/922 |
| 5,236,362 | A | 8/1993 | Cohen et al. | 433/228.1 |
| 5,252,629 | A | 10/1993 | Imai et al. | 523/118 |
| 5,267,859 | A | 12/1993 | Discko, Jr. | 433/89 |
| 5,279,800 | A | 1/1994 | Berr, Jr. | 422/300 |
| 5,284,632 | A | 2/1994 | Kudla et al. | 422/297 |
| 5,294,413 | A | 3/1994 | Riihimaki et al. | 422/297 |
| 5,322,440 | A | 6/1994 | Steele | 433/90 |
| 5,324,273 | A | 6/1994 | Discko, Jr. | 604/240 |
| 5,340,551 | A | 8/1994 | Berry, Jr. | 422/300 |
| 5,346,677 | A | 9/1994 | Risk | 422/297 |
| 5,360,877 | A | 11/1994 | Hwang et al. | 525/423 |
| D353,673 | S | 12/1994 | Discko, Jr. et al. | D24/152 |
| 5,384,103 | A | 1/1995 | Miller | 422/310 |

FOREIGN PATENT DOCUMENTS

| | | |
|---|---|---|
| CA | 1131827 | 9/1982 |
| CA | 1140939 | 2/1983 |
| CA | 1151667 | 8/1983 |
| CA | 1153391 | 9/1983 |
| CA | 1155141 | 10/1983 |
| CA | 1175196 | 9/1984 |
| CA | 1183144 | 2/1985 |
| CA | 1185982 | 4/1985 |
| CA | 1189996 | 7/1985 |
| CA | 1200555 | 2/1986 |
| CA | 1202749 | 4/1986 |
| CA | 1210777 | 9/1986 |
| CA | 1219990 | 3/1987 |
| CA | 1227202 | 9/1987 |

| | | |
|---|---|---|
| CA | 1235423 | 4/1988 |
| CA | 1242213 | 9/1988 |
| CA | 1248126 | 1/1989 |
| CA | 1258465 | 8/1989 |
| CA | 2002017 | 5/1990 |
| CA | 1270846 | 6/1990 |
| CA | 2005912 | 6/1990 |
| CA | 2006431 | 6/1990 |
| CA | 2006432 | 6/1990 |
| CA | 2006433 | 6/1990 |
| CA | 2006434 | 6/1990 |
| CA | 2004624 | 7/1990 |
| CA | 2026009 | 7/1990 |
| CA | 1272735 | 8/1990 |
| CA | 2008895 | 8/1990 |
| CA | 2009471 | 8/1990 |
| CA | 2012824 | 9/1990 |
| CA | 2014027 | 10/1990 |
| CA | 2014359 | 10/1990 |
| CA | 1276168 | 11/1990 |
| CA | 1276648 | 11/1990 |
| CA | 1277070 | 11/1990 |
| CA | 2054747 | 11/1990 |
| CA | 2010210 | 12/1990 |
| CA | 2018728 | 12/1990 |
| CA | 2019410 | 12/1990 |
| CA | 2054710 | 12/1990 |
| CA | 2054757 | 12/1990 |
| CA | 1281734 | 3/1991 |
| CA | 2026467 | 3/1991 |
| CA | 1283121 | 4/1991 |
| CA | 1283663 | 4/1991 |
| CA | 2027887 | 4/1991 |
| CA | 2042587 | 4/1991 |
| CA | 2028728 | 5/1991 |
| CA | 2032556 | 6/1991 |
| CA | 2033405 | 7/1991 |
| CA | 2035650 | 8/1991 |
| CA | 2026417 | 9/1991 |
| CA | 2038332 | 9/1991 |
| CA | 1290766 | 10/1991 |
| CA | 2045762 | 12/1991 |
| CA | 2046373 | 1/1992 |
| CA | 1296015 | 2/1992 |
| CA | 2049725 | 3/1992 |
| CA | 2061230 | 8/1992 |
| CA | 2061539 | 8/1992 |
| CA | 2041828 | 11/1992 |
| CH | 227 363 | 1/1984 |
| DE | 1 003 448 | 8/1958 |
| DE | 2 126 419 | 12/1971 |
| DE | 141 667 | 5/1980 |
| DE | 154 945 | 6/1982 |
| DE | 209 358 | 4/1984 |
| DE | 208 365 | 5/1984 |
| DE | 214 381 | 10/1984 |
| DE | 229 140 | 10/1985 |
| DE | 244 748 | 4/1987 |
| DE | 35 36 076 | 4/1987 |
| DE | 35 36 077 | 4/1987 |
| DE | 248 598 | 8/1987 |
| DE | 261 365 | 10/1988 |
| DE | 277 078 | 3/1990 |
| DE | A-227 689 | 4/1990 |
| DE | 277 689 | 4/1990 |
| DE | 279 667 A1 | 6/1990 |
| DE | 279 667 | 8/1990 |
| DE | 295 758 | 11/1991 |
| DE | 4217761 | 5/1992 |
| DE | 41 41 174 | 6/1992 |
| DE | 41 09 048 | 9/1992 |
| DE | 42 17 761 | 2/1993 |
| DE | 4129613 | 3/1993 |
| EP | 037 759 | 10/1981 |
| EP | 120 559 | 1/1983 |
| EP | A-0 104 491 | 4/1984 |
| EP | 104 491 | 4/1984 |
| EP | 115 410 | 4/1984 |
| EP | 115 948 | 8/1984 |
| EP | 188 752 | 12/1984 |
| EP | A-0 188 752 | 7/1986 |
| EP | 212 193 | 3/1987 |
| EP | 0 212 193 | 3/1987 |
| EP | 219 058 | 4/1987 |
| EP | 277 413 | 10/1988 |
| EP | 0 356 868 | 3/1990 |
| EP | 356 868 | 3/1990 |
| GB | 1 304 987 | 1/1973 |
| GB | 2 045 269 | 10/1980 |
| GB | 2 199 839 | 7/1988 |
| JP | 3-27308 | 6/1989 |
| JP | 1-143846 | 6/1989 |
| JP | 1-254727 | 10/1989 |
| JP | 4-4219 | 1/1992 |
| JP | 4-120540 | 4/1992 |
| SU | 52106 | 4/1937 |
| SU | 311 637 | 8/1971 |
| SU | 311 638 | 8/1971 |
| SU | 349 396 | 9/1972 |
| SU | 545 353 | 2/1977 |
| SU | 549 150 | 3/1977 |
| SU | 1 050 706 | 4/1982 |
| SU | 1 510 131 | 11/1986 |
| WO | 90/15083 | 12/1990 |
| WO | 90/15084 | 12/1990 |
| WO | 91/03502 | 3/1991 |
| WO | 93/10176 | 5/1993 |

OTHER PUBLICATIONS

Klee et al, Polymer Bulletin 27 (1992); pp. 511–517.
Chemical Abstract, vol. 89, No. 18, Oct. 30, 1978, Columbis OH, US; Abstract No. 148211C; p. 71, Column 2; abstract & Lakokras Mater. IKH, Primen., No. 4, 1978, pp. 50–52.
Dusek et al; American Chemical Society (1984) Transesterification and Gelation of Polyhydroxy Esters Formed from Diepoxides and Dicarboxylic Acids.
Hartel et al; (Nov. 1984) Zur Synthese linearer Additionspolymere aus Diandiglycidether und Dicarbonsauren.
Klee; Acta Polymer 44, 163–167 (1993); Synthesis and investigation of α, w–methacryloyl poly (epoxide–carboxylic acid and α, w–methacryloyl poly (epoxide–phenol)—macromonomers.
J. Klee et al, Acta Polymer 42 (1991) 17–20.
Fukushima et al; Dental Materials Journal 4(1) : pp. 33–39 (1985) : Application of Functional Monomers for Dental Use (Part 9) Sysntheses of Succinoxy Methacrylates and Their Adhesion to Polished and Etched Tooth Surfaces.
Lin et al; Journal of Polymer Science; Part A: Polymer Chemistry, vol. 30, 1941–1951 (1992).
Allard et al; Journal of Polymer Science: Polymer Chemistry Edition, vol. 22, 3827–3842 (1984).
Hage et al; American Chemical Society (1986) Poly (acrylourethane) —Polyepoxide Semi–interpenetrating Networks Formed by Electron–Beam Curing.
Dubuisson et al; Rheol. Acta 20, 463–470 (1981).
Klee; Acta Polymer., 45, 73–82 (1994) Telechelic prepolymers and macromonomers by step growth processes.
John Wiley & Sons; Encyclopedia of Polymer Science and Engineering, vol. 8, Identification to Lignin.

* cited by examiner

POLYMERIZABLE COMPOUNDS AND COMPOSITIONS

This is a continuation of application Ser. No. 08/359,217, filed Dec. 19, 1994, now abandoned, which is a continuation-in-part of U.S. patent application Ser. No. 08/231,535 filed Apr. 22, 1994, abandoned, which is a continuation-in-part of U.S. patent application Ser. No. 08/217,998 filed Mar. 25, 1994, now U.S. Pat. No. 5,624,976, which is a continuation-in-part of U.S. patent application Ser. No. 08/067,774 filed May 26, 1993, abandoned.

The invention relates to polymerizable macromonomers and dental and medical compositions containing polymerizable macromonomers. The invention provides macromonomers for dental compositions and a process for preparing them. Dental/medical compositions which include macromonomers of the invention have a high adhesion to hard dental tissue and low volumetric shrinkage.

It is an object of the invention to provide an esterified macromonomer within the scope of the general formula:

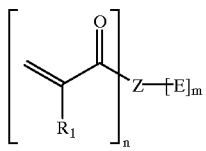

wherein Z is an organic moiety, $R_1$ is hydrogen or a substituted or unsubstituted alkyl having from 1 to 12 carbon atoms, oxyalkyl having from 1 to 12 carbon atoms, alkenyl having from 2 to 12 carbon atoms, cycloalkyl having from 5 to 12 carbon atoms, aryl having from 6 to 12 carbon atoms or aralkyl having from 7 to 12 carbon atoms. Each E independently is a hydroxyl group, an organic ester moiety or an inorganic ester moiety and at least one E is a ester containing moiety. n and m each independently is an integer from 2 to 12.

It is the object of the invention to provide an esterified macromonomer obtainable by esterification of at least a portion of the —OH groups of a macromonomer having at least one terminal double bond with at least one derivative of an inorganic or organic acid which introduces pendant groups exhibiting at least one acid moiety selected from the group of consisting of —COOH, —$PO_3H_2$, —$SO_3H$, —$BO_2H$ and salts thereof. The number of the acid moieties is chosen such that a polymer obtained by polymerizing said monomers has an adhesive strength to dentine of at least 2 MPa.

Prior Art dental/medical compositions such as cements are either water-based ionic cements or resin based materials. The water-based cements have the advantage of a modest adhesion to hard tooth tissues and of a high fluoride ion release from inorganic filler material. They have the disadvantage of high water solubility, low abrasion resistance and an excessive opacity. The resin-based materials have the advantage of excellent mechanical properties, a suitable opacity and low water solubility. They have the disadvantage of a lack of adhesion, a very poor release of fluoride ions from an inorganic filler and a high volumetric shrinkage.

Engelbrecht et al in U.S. Pat. No. 4,806,381 discloses Polymerizable Compounds Containing Acid and Acid Derivatives, Mixtures Containing the Same, and Use Thereof. Blackwell et al in U.S. Pat. No. 4,816,495 discloses Biologically Compatible Adhesive Visible Light Curable Compositions.

These disadvantages of prior art dental compounds and compositions are overcome by the novel and nonobvious compounds and compositions of the invention.

BRIEF DESCRIPTION OF THE INVENTION

An esterified macromonomer within the scope of the general formula (I):

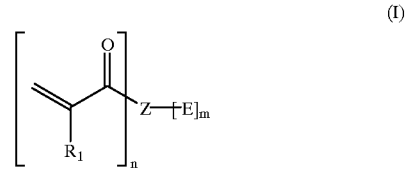

wherein Z is an organic moiety. $R_1$ is hydrogen or a substituted or unsubstituted alkyl having from 1 to 12 carbon atoms, oxyalkyl having from 1 to 12 carbon atoms, alkenyl having from 2 to 12 carbon atoms, cycloalkyl having from 5 to 12 carbon atoms, aryl having from 6 to 12 carbon atoms or aralkyl having from 7 to 12 carbon atoms. Each E independently is a hydroxyl group, an organic ester moiety, or an inorganic ester moiety. At least one E is an ester moiety. n and m each independently is an integer from 2 to 12. The esterified macromonomer is obtainable by esterification of at least a portion of the —OH groups of a macromonomer having at least one terminal double bond with at least one derivative of an inorganic or organic acid which introduces pendant groups exhibiting at least one acid moiety selected from the group of consisting of —COOH, —$PO_3H_2$, —$SO_3H$, —$BO_2H$ or salts thereof. The number of the acid moieties is chosen such that a polymer obtained by polymerizing those monomers has an adhesive strength to dentine of at least 2 MPa.

DETAILED DESCRIPTION OF THE INVENTION

The invention provides macromonomers esterfied, with organic acids or inorganic acids or derivatives thereof. The esterified macromonomers are useful in composition with or without water, such as water free self-adhesive dental/medical composite. The dental/medical composite comprises a modified macromonomer, and/or di- or poly(methacrylates) containing phosphoric acid ester groups or salts thereof, polymerizable monomers, acid-reactive and/or reactive and/or non-reactive fillers, diluents, polymerization initiators and stabilizers. Composition in accordance with the invention include polymerization initiators, such as thermal initiators, redox initiators and/or photoinitiators. The new adhesive dental composite develops adhesion to dentine of about 4 MPa. Fillers of high X-ray absorbence provide radio-opacity values greater than that of the same thickness of aluminium.

Preparation of Epoxide-macromonomers

Macromonomers in accordance with the invention are produced by chemical modification of macromonomers containing hydroxyl groups. Macromonomer containing hydroxyl groups useful for making esterified macromonomer in accordance with the invention are described for example in Polym. Bull. 27 (1992) 511–517, Acta Polym. 42 (1991) 17–20 and DE 4217761.8 incorporated herein by reference. Preferred polymerizable compounds for use in compositions in accordance with the invention are within the scope of general formulas M1–M12 as follows:

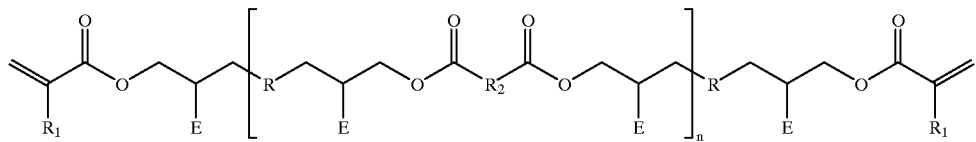
M-1
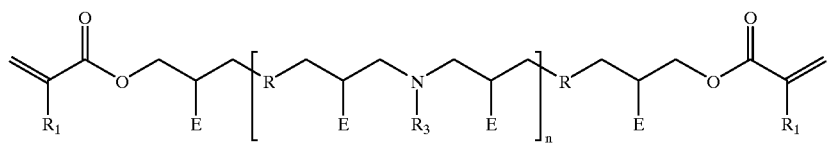
M-2
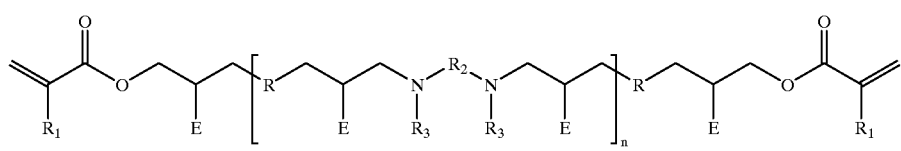
M-3
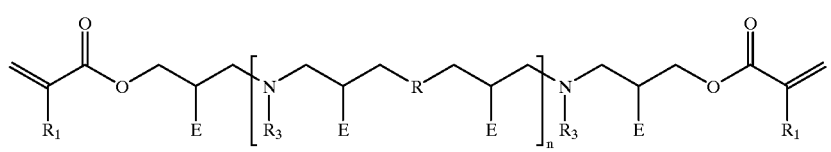
M-4
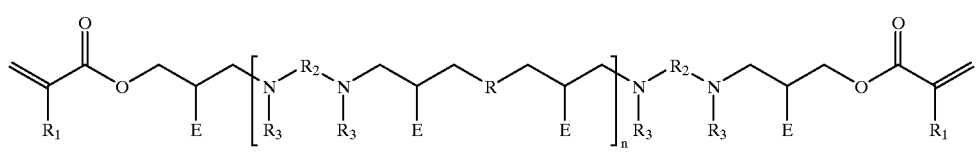
M-5
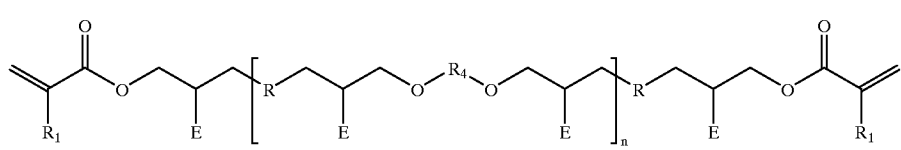
M-6
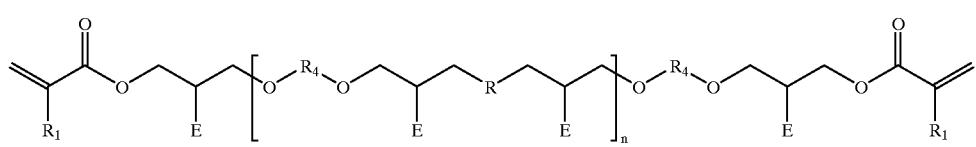
M-7
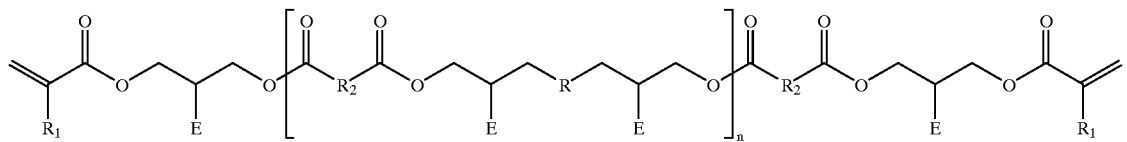
M-8
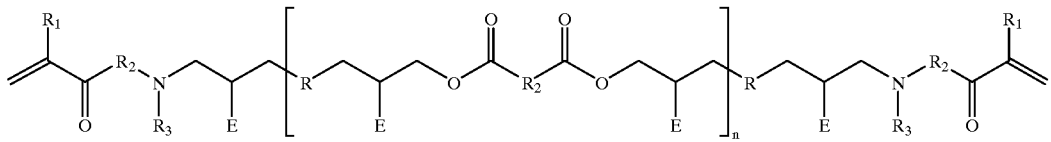
M-9
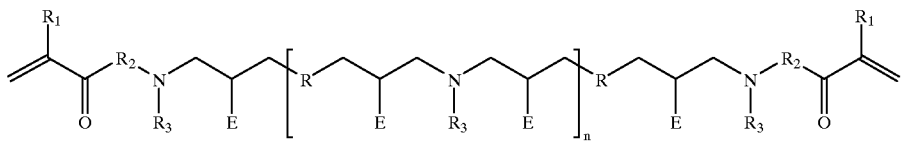
M-10

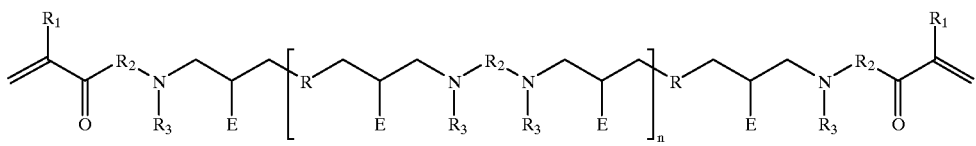

M-11

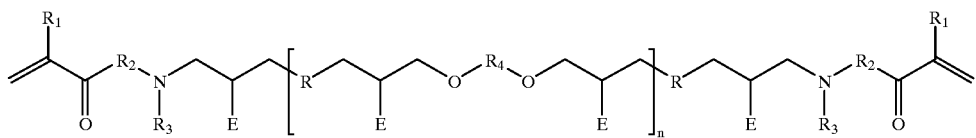

M-12 wherein

- each E independently is a hydroxyl group, an organic ester moiety or an inorganic ester moiety,
- at least one E is an ester moiety,
- R is a diether or a diester containing moiety or tertiary amine,
- $R_1$ is hydrogen or a substituted or unsubstituted alkyl having from 1 to 12 carbon atoms, oxyalkyl having from 1 to 12 carbon atoms, alkenyl having from 2 to 12 carbon atoms, cycloalkyl having from 5 to 12 carbon atoms, aryl having from 6 to 12 carbon atoms or aralkyl having from 7 to 12 carbon atoms,
- $R_2$ is a difunctional substituted or unsubstituted alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms,
- $R_3$ is hydrogen or a substituted or unsubstituted alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms,
- $R_4$ is a substituted or unsubstituted aryl having from 6 to 12 carbon atoms,
- and n is an integer of at least 1.

Preferably R is a moiety within the scope of the general formulas:

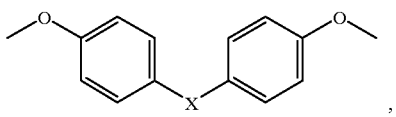

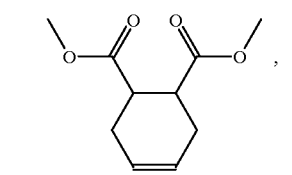

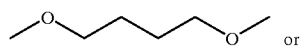 or

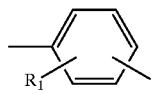

(according to R of the foreclosures)

wherein X is $C(CH_3)_2$, —$CH_2$—, —O—, —S—, —CO—, or —$SO_2$—.

Preferably R4 is a moiety within the scope of the general formulas:

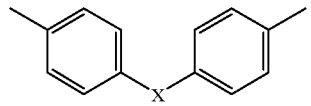

or

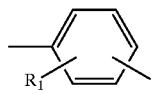

wherein X is $C(CH_3)_2$, —$CH_2$—, —O—, —S—, —CO—, —$SO_2$—.

Preferably E is a hydroxyl group, an ester moiety, a boric acid moiety, a sulfuric acid moiety or a phosphoric acid moiety.

Macromonomers within the scope of general formula M-1 are synthesized in two steps. At first an oligomer mixture is obtained by reaction of an α,β-unsaturated acids with excessive amounts of a diepoxide, such as bisphenol-A diglycidyl ether (DGEBA), bisphenol-F diglycidyl ether (DGEBF), butanediol diglycidyl ether (BDODGE), tetrahydro terephtalic acid diglycidyl ether or diglycidyl aniline. This mixture contains the bis-ester of the diepoxide along with the mono-ester and unreacted diepoxide as governed by the ratio of the diepoxide and the unsaturated acid. The formation of macromonomers follows in a second reaction of the previous reacted oligomers with dicarboxylic acids to M-1 (DE 4217761.8).

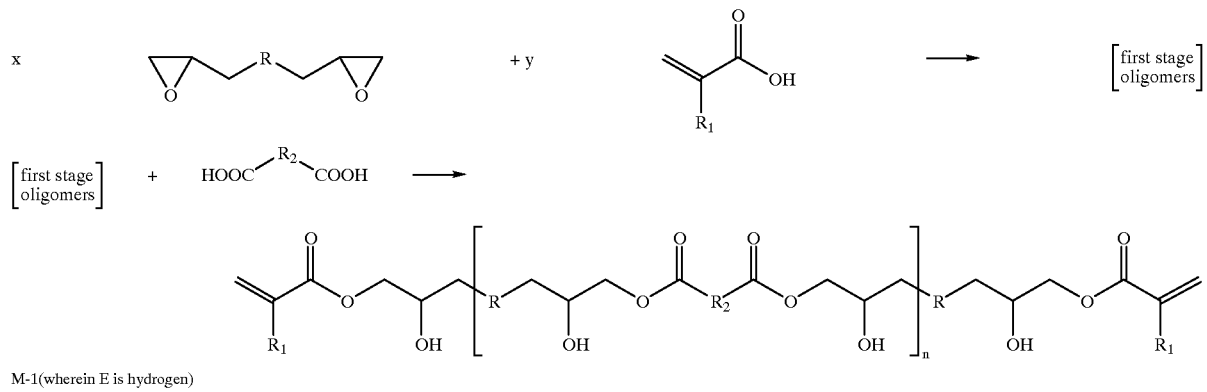

M-1(wherein E is hydrogen)

Instead of dicarboxylic acids in the second step also primary monoamines were used which react to macromonomers M-2, disecondary diamines which react to macromonomers M-3, (J. Klee et. al. Polym. Bull. 27 (1992) 511–517, DD 279667) and bisphenols which react to macromonomers M-6.

During the epoxide ring cleavage by carboxylic acids an amount equal to approximately 20 percent by weight of the epoxide groups is opened to the corresponding primary alcohols:

Consequently, macromonomers M-1, M-2, M-3 and M-6 wherein each E is hydrogen contain both types of molecules having primary and/or secondary alcohol units.

The resulting macromonomers are viscous liquids or solids which are soluble in THF, CHCl$_3$ and DMF. Their glass transition temperatures are relatively low (between 0 and 50° C.) depending on the nature of the comonomer and the molecular mass of the macromonomers.

The degree of polymerisation $P_n$ and the macromonomer value n depends on the mol ratio of the monomers, the diepoxide and the comonomers and were calculated by $$P_n = \frac{1+r}{1-r} \text{ and } n = \frac{r}{1-r},$$

respectively using r=z/x. That means each macromonomer M is a definite mixture of a series of homologous oligomers (n=1,2,3,4,5, . . . ) and contains a certain amount of the molecule (n=0).

Macromonomers M-5 wherein each E is hydrogen are prepared by one-step reaction of the diepoxides, disecondary diamines and 2,3-epoxypropyl-(meth)acrylate according to the following equation:

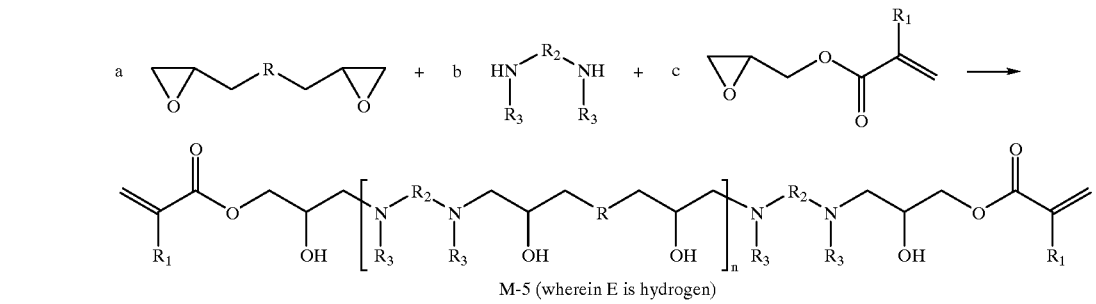

M-5 (wherein E is hydrogen)

A second route to obtain macromonomers M-5 wherein each E is hydrogen is a two-step reaction. In the first step the diepoxide is reacted with the disecondary diamine to an α,ω-terminated prepolymer. In the second step the obtained prepolymer is reacted with 2,3-epoxypropyl-(meth) acrylate (DD 277689, J.Klee, H.-H. Hörhold, H.Schütz, Acta Polym. 42 (1991) 17–20).

Instead of disecondary diamines in the second step also were used primary monoamines react to macromonomers M-4, bisphenols react to macromonomers M-7 or dicarboxylic acids react to macromonomers M-8.

Macromonomers M-9 wherein each E is hydrogen are prepared by reaction of diepoxides, dicarboxylic acids and aminoalkyl (meth)acrylates according to the following equation:

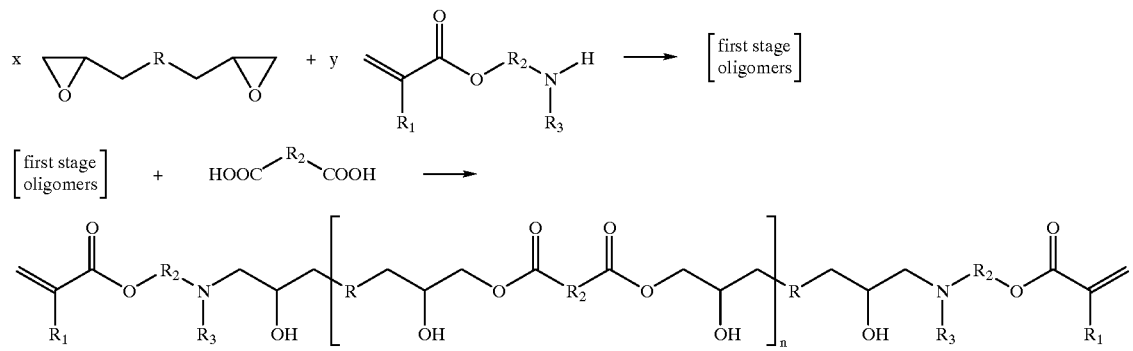

Instead of dicarboxylic acids, primary monoamines were used to prepare macromonomers M-10, disecondary diamines were used to prepare macromonomers M-11, bisphenols were used to prepare macromonomers M-12.

Specific macromonomers M-1 to M-12 representing molecules of n=0, n=1 or n=2 may be isolated from the mixture by fractionated precipitation or by chromatography and subjected to esterification as described.

Esterification of Macromonomers

The reaction of epoxide macromonomers M-1 to M-12 with organic acids or inorganic acids or derivatives thereof leads to macromonomers having ester moieties.

As derivatives of organic acids preferably were used succinic acid anhydride, maleic acid anhydride, dichloromaleic acid anhydride, dimethyl maleic acid anhydride, malonic acid anhydride, aconit acid anhydride, adipic acid anhydride, 3,3-tetramethylen glutaric acid anhydride, cyclohexen-1,2 acid anhydride, nadinic acid anhydride, phthalic acid anhydride, trimellitic acid anhydride, 2-sulfobenzoic acid anhydride, 2-sulfo succinic acid anhydride, phthalic acid anhydride p-(O-phosphat), phthaloyl-chloride, succinic acid dimethyl ester.

As derivatives of inorganic acids preferably were used phosphorous penta chloride, phosphorous trichloride, phosphorous oxychloride, sulfuryl chloride, thionyl chloride, phosphor thionyl chloride, boric acid anhydride, boron trichloride.

It is possible to synthesize the esterified macromonomers without using any catalysts in the cases of M-2 to M-5, M-10, M11 (n>0). These macromonomers contain the catalytic active amine in the backbone of the molecule. The use of catalysts such as tertiary amines or quarterly ammonium salts is possible and in the case of esterification of M-1, M-6, M-7, M-8, M-9 and M-12 necessary.

The esterification of the macromonomer hydroxyl groups is carried out in pure substance or in diluted solutions. Preferably, solvents such as tetrahydro furane, dioxane, or polymerizable monomers such as triethylenglycol bismethacrylate, diethylenglycol bismethacrylate, dioxolan bismethacrylate, vinyl-, vinylen- or vinyliden-, acrylate- or methacrylate substituted spiroorthoesters and 2,2-Bis[p-(acryloxyethoxy)phenyl]propane are present during esterification of the macromonomers. The temperature is in the preferred range of 60° C. to 120° C.

Dental/medical Application

A dental/medical composite, a dental/medical sealant, a dental/medical adhesive and a dental/medical primer have been developed comprising a modified α,ω-(meth) acryloyl terminated macromonomer notably a di- or poly(meth) acrylate monomer having phosphorous ester groups or salts thereof, polymerizable monomers, fillers, polymerization initiators and stabilizers.

As di- or poly(meth)acrylate monomer having phosphorous ester groups and salts thereof are employed pentaerythrit triacrylate monophosphate, dipentaerythrit pentaacrylate monophosphate, glycerol di(meth)acrylate monophosphate, triethylenglycol (meth)acrylate monophosphate.

As organic polymerizable monomers were used mono- and polyfunctional (meth)acrylates, such as polyalylenoxide di- and poly(meth)acrylates, urethane di- and poly(meth) acrylates, vinyl-, vinylen- or vinyliden-, acrylate- or methacrylate substituted spiroorthoesters, spiroorthocarbonates or bicyloorthoesters. Preferably were used diethylenglycol dimethacrylate, triethylenglycol dimethacrylate, 3,(4),8,(9)-di-methacryloyloxymethyltricyclodecane, dioxolan bismethacrylate, glycerol trimethacrylate, furfuryl methacrylate in a content of 5 to 80 wt-%.

As polymerization initiators are used thermal initiators, redox initiators and/or photo initiators in a content of 0,001 to 3 wt-%.

Thermal initiators are initiators such as peroxides, peresters, perketals, peroxy carbonates, hydroxyperoxides, persulfates and azo compounds preferably dibenzoyl peroxide, cumol hydroperoxide, diisopropyl peroxycarbonate, dipotassium persulfate, azobisisobutylonitril.

Preferred redox initiator systems for use in compositions in accordance with the invention are peroxide/amine systems, such as peracid/amine, perester/amine, perketal/amine, peroxycarbonate/amine and hydroxyperoxide/amine systems; peroxide/metal ion salts, such as ascorbic acid/peroxide/metal ion compounds, (thio)barbituric acid/peroxide/metal ion compounds, metal ion compounds/sulfinates, metal ion compounds/(thio)barbituric acid; transition metal carbonyl compounds and halogenids of organic compounds; boralkyl compounds, peroxysulfates and thiols. Most preferred redox-initiators are benzoylperoxide/N,N-bis-(β-hydroxyethyl)-p-toluidine, benzoylperoxide/N,N-bis-(β-hydroxyethyl)-p-benzoic acid ethylester, benzoylperoxide/tributylamine, cumol hydroperoxide/N, N-bis-(β-hydroxyethyl)-p-toluidine, diisopropyl peroxycarbonate/dimethylbenzylamine.

Preferred photoinitiators for use in polymerizable compositions in accordance with the invention which include macromonomers with the scope of general formulas M-1 through M-12 are camphorquinone, benzophenone and 2,2-dimethylbenzylketal.

Preferred fillers for use in compositions in accordance with the invention include inorganic compounds, such as $La_2O_3$, $ZrO_2$, $BiPO_4$, $CaWO_4$, $BaWO_4$, $SrF_2$, $Bi_2O_3$, glasses and/or organic fillers, such as polymer granulate. Dental/medical composite compositions of the invention preferably include filler in an amount from about 50 to about 85 percent by weight. Dental/medical adhesive compositions of the invention preferably include filler in an amount from about 50 to about 65 percent by weight. Dental/medical sealant compositions of the invention preferably include filler in an amount from about 10 to about 50 percent by weight.

Dental/medical composite compositions, adhesives and sealant of the invention include one-component and two-component paste/paste and powder/liquid-material which is to be mixed immediately before use.

Shrinkage of composite compositions of the invention is preferably less than 4.5 and more preferably less than 1.5 percent by volume. Adhesive dental composite compositions of the invention containing radio-opaque fillers preferably provide a radio-opacity of at least 1.5 mm/mm Al, more preferably at least 3 to 7 mm/mm Al, and most preferably at least 7 mm/mmAl.

The self-adhesive dental/medical composites compositions in accordance with a preferred embodiment of the invention have a fluoride release of at least 1 $\mu g/cm^2$, more preferably at least 1–3 $\mu g/cm^2$, and most preferably at least 3–10 $\mu g/cm^2$.

Self-adhesive dental/medical composites compositions in accordance with a preferred embodiment of the invention have an opacity of at least 40%, more preferably at least 20–40%, and most preferably at least 5–20%.

The setting time of the adhesive dental/medical adhesive compositions in accordance with a preferred embodiment of the invention at 37° C. is between 1 minute and 60 minutes, more preferably between 5 and 30 minutes and most preferably between 2 and 5 minutes. The setting time of adhesive compositions in accordance with a preferred embodiment of the invention at 23° C. is preferably between 10 minutes and 300 minutes more, preferably between 5 and 100 minutes and most preferably between 5 and 20 minutes.

Dental/medical composition in accordance with the invention is characterised by having an adhesion to dentine of at least 2 MPa; a fluoride release of at least 1 $\mu g$ $F^-$ per week and per $cm^2$ of the exposed surface of the composition; an opacity of at least $C_{0,7}$=40%; and a compressive strength of at least 200 Mpa.

In the following examples bond strength to dentin is measured using extracted human teeth. The teeth used for the shear bond strength test are treated in 1% sodium hypochlorite for one hour and then stored in distilled water in a refrigerator at about 4° C. until needed. The teeth are washed with water, mechanically sanded with 320 grit carborundum paper until a flat dentin surface is exposed.

The teeth are then individually blown dry with compressed dry air to ensure the dentin surface is free from noticeable moisture. A small plastic straw with 5 mm inner diameter and 2 to 3 mm in length is filled with the polymerizable composition being tested and seated on the dentin so as to form a post without pressure. The upper open end of the straw is covered with a thin film and cured. The specimens are then stored in distilled water at 37° C. for 24 hours. The teeth are then vertically mounted in a 7 cm ring using gypsum to provide a base for testing with the post at right angles thereto. The mounted specimens are then loaded in shear in an Zwick device model number 1455 manufactured by Zwick GmbH for measurement of adhesion of the post to dentin at 1 mm/minute crosshead speed. The load is applied parallel to the prepared tooth surface and at right angles to the post until fracture occurred. The shear bond strength is then calculated.

In the examples Fluoride Release is measured by making three 1×20 mm (diameter) discs of each material. Each disc is placed in 25 ml water stored for a week at 37° C. Using an ion selective electrode, the fluoride concentration in mg $F^-/cm^2$ is determined for each disc. The average value of the three discs is recorded.

In the Examples compressive strength is measured according to ISO 9917, EN 29917; flexural strength is measured according to ISO 4049, EN 24049; elastic modulus is measured according to ISO 4049, EN 24049; opacity is measured according to ISO 9912, EN 29912; IR spectra are measured using a Fourier transformation Infra Red spectrometer at 23° C.

REFERENCE EXAMPLE 1

The macromonomer of formula M-1 wherein n is 1, R is —$OC_6H_4$—$C(CH_3)_2$—$C_6H_4O$—, $R_1$ is —$CH_3$, $R_2$ is —$(CH_2)_4$— is referred to hereinafter as macromonomer M-1A and is prepared by reacting 150.000 g (0.441 mol) bisphenol-A diglycidyl ether, 32.200 g (0.220 mol) adipic acid and 2,000 g triethylbenzylammoniumchloride for four hours at 80° C. while stirring. To the obtained glycidyl terminated prepolymer are added 37.900 g (0.441 mol) methacrylic acid and 0.444 g 2,6-di-tert.-butyl-p-cresol and are reacted for another four hours at 80° C. The methacrylate terminated macromonomer is soluble in organic solvents such as chloroform, DMF and THF. In the IR-spectrum no absorption of epoxide groups at $\nu$=915 and 3050 $cm^{-1}$ is observed. Absorption of ester groups is seen at $\nu$=1720 $cm^{-1}$. In the $^1H$ NMR spectrum are found signals of the olefinic double bond at $\delta_{(CH2=)}$=6,137/6,119/6,115 ppm and at $\delta_{(CH2=)}$=5,587/5,582/5,555/5,548 ppm.

REFERENCE EXAMPLE 2

Preparation of the Macromonomer of Formula M-1B Wherein E is Hydroxyl, n is 1, R is —$O(CH_2)_4O$—, $R_1$ is —$CH_3$, $R_2$ is —$(CH_2)_4$—

200.00 g (0.99 mol) butanediol diglycidyl ether, 72.26 g (0.49 mol) adipic acid, 85.13 g (0.99 mol) methacrylic acid, 4.72 g triethylbenzylammoniumchloride and 0.60 g 2,6-di-tert.-butyl-p-cresol are stirred together and heated for four hours at 90° C. The obtained methacrylate terminated macromonomer is soluble in organic solvents such as chloroform, DMF and THF. In the IR-spectrum no absorption of epoxide groups at 915 and 3050 $cm^{-1}$ is observed. Absorption of ester groups is seen at 1720 $cm^{-1}$. The viscosity measured with a Bohlin rheometer is $\theta_{dyn}$=3.3 Pas (25° C.).

REFERENCE EXAMPLE 3

Preparation of the Macromonomer of Formula M-1F Wherein E is Hydroxyl, n is 1, R is —$OC_6H_4$—$CH_2$—$C_6H_4O$—, $R_1$ is —$CH_3$, $R_2$ is —$(CH_2)_4$—

100.00 g (0.32 mol) bisphenol-F diglycidyl ether, 23.39 g (0.16 mol) adipic acid, 27.56 g (0.32 mol) methacrylic acid, 65.47 g triethylenglycol dimethacrylate, 1.53 g triethylbenzylammoniumchloride and 0.30 g 2,6-di-tert.-butyl-p-cresol are stirred together and heated for four hours at 90° C. The obtained methacrylate terminated macromonomer is soluble in organic solvents such as chloroform, DMF and THF. In the IR-spectrum no absorption of epoxide groups at 915 and 3050 cm$^{-1}$ is observed. Absorption of ester groups is seen at 1720 cm$^{-1}$. The viscosity measured with a Bohlin rheometer is $\eta_{dyn}$=3.6 Pas (25° C.).

REFERENCE EXAMPLE 4

Preparation of the Macromonomer of Formula M-3 Wherein E is Hydroxyl n is 1, R is —OC$_6$H$_4$—C(CH$_3$)$_2$—C$_6$H$_4$O—, R$_1$ is —CH$_3$, R$_2$ is —(CH$_2$)$_4$O(CH$_2$)$_4$—, R$_3$ is C$_6$H$_5$CH$_2$—

150,000 g (0,441 mol) bisphenol-A diglycidyl ether, 37,935 g (0.441 mol) methacrylic acid, 2,000 g triethylbenzylammonium chloride, 1,115 g 2,6-di-tert.-butyl-p-cresol (BHT) and 111,695 g triethylenglycol dimethacrylate were homogeneously mixed while heating. The mixture was kept for two hours at 90° C. After this time 75,020 g (0.221 mol) N,N'-dibenzyl-5-oxanonanediamine-1,9 were added to the mixture while stirring and kept for additional two hours at 90° C. The obtained methacrylate terminated macromonomer is soluble in organic solvents such as chloroform, DMF and THF. No absorption of epoxide groups at 915 and 3050 cm$^{-1}$ is observed in the IR-spectrum. Absorption of ester groups were found at 1720 cm$^{-1}$.

REFERENCE EXAMPLE 5

Preparation of the Macromonomer of Formula M-5 Wherein E is Hydroxyl, n is 1, R is —OC$_6$H$_4$—C(CH$_3$)$_2$—C$_6$H$_4$O—, R$_1$ is —CH$_3$, R$_2$ is —(CH$_2$)$_4$O(CH$_2$)$_4$—, R$_3$ is C$_6$H$_5$CH$_2$—

20,000 g (58.75 mmol) bisphenol-A diglycidyl ether and 40,012 g (117.50 mmol) N,N'-dibenzyl-5-oxanonanediamine-1,9 are homogeneously mixed while heating. The mixture is kept for two hours at 90° C. After this time 16,704 g (117.50 mmol) 2,3-epoxypropyl methacrylate is added to the mixture while stirring and the mixture is for another two hours at 90° C. The obtained methacrylate terminated macromonomer is soluble in organic solvents such as chloroform, DMF and THF. In the IR-spectrum no absorption of epoxide groups at 915 and 3050 cm$^{-1}$ is observed.

REFERENCE EXAMPLE 6

Preparation of the Macromonomer of Formula M-5 Wherein E is Hydroxyl, n is 0, R$_1$ is —CH$_3$, R$_2$ is —(CH$_2$)$_4$O(CH$_2$)$_4$—, R$_3$ is C$_6$H$_5$CH$_2$—

50,000 g (146.83 mmol) N,N'-dibenzyl-5-oxanonanediamine-1,9, 41,750 g (293.67 mmol) 2,3-epoxypropyl methacrylate and 0.213 g BHT are homogeneously mixed while heating. The mixture is kept for two hours at 90° C. The obtained methacrylate terminated macromonomer is soluble in organic solvents such as chloroform, DMF and THF. In the IR-spectrum no absorption of epoxide groups at 915 and 3050 cm$^{-1}$ are observed.

REFERENCE EXAMPLE 7

Preparation of the Macromonomer of Formula M-6 Wherein E is Hydroxyl, n is 1, R is —OC$_6$H$_4$—C(CH$_3$)$_2$—C$_6$H$_4$O—, R$_1$ is —CH$_3$, R$_4$ is —C$_6$H$_4$—C(CH$_3$)$_2$—C$_6$H$_4$—

150,000 g (0.441 mol) bisphenol-A diglycidyl ether, 50,299 g (0.220 mol) 2,2-bis-(4-hydroxy-phenyl)propane, 37,901 g (0.441 mol) methacrylic acid, 102,086 g triethylenglycol dimethacrylate, 2.000 g triethylbenzylammoniumchloride and 0.959 g 2,6-di-tert.-butyl-p-cresol are heated for four hours at 80° C. The obtained methacrylate terminated macromonomer is soluble in organic solvents such as chloroform, DMF and THF. In the IR-spectrum no absorption of epoxide groups at 915 and 3050 cm$^{-1}$ is observed. Absorption of ester groups is found at 1720 cm$^{-1}$.

REFERENCE EXAMPLE 8

Preparation of the Macromonomer of Formula M-7 Wherein E is Hydroxyl, n is 1, R is —OC$_6$H$_4$—C(CH$_3$)$_2$—C$_6$H$_4$O—, R$_1$ is —CH$_3$, R$_4$ is —C$_6$H$_4$—C(CH$_3$)$_2$—C$_6$H$_4$—

100,000 g (0.294 mol) bisphenol-A diglycidyl ether, 134,235 g (0.588 mol) 2,2-bis-(4-hydroxy-phenyl)propane, 83,520 g (0.588 mmol) 2,3-epoxypropylmethacrylate, 2,000 g triethylbenzylammonium chloride, 0.794 g 2,6-di-tert.-butyl-p-cresol (BHT) and 79,439 g triethylenglycol dimethacrylate are homogeneously mixed while heating. The mixture is kept for two hours at 80° C. The obtained methacrylate terminated macromonomer is soluble in organic solvents such as chloroform, DMF and THF. No absorption of epoxide groups at 915 and 3050 cm$^{-1}$ is observed in the IR-spectrum. Absorption of ester groups is found at 1720 cm$^{-1}$.

Example 1

The hydroxyl groups of macromonomer M-1A made by following the procedure of reference example 1 are esterified by adding 16,023 g (160.13 mmol) succinic anhydride to 56,900 g of a macromonomer-triethylenglycol dimethacrylate mixture containing 40,000 g (40.03 mmol) macromonomer M-1A and 16.9 g of triethylenglycol dimenthacrylate) while stirring for two hours at 90° C. In the IR-spectrum the esterified macromonomer containing dicarboxylic half ester units shows no absorption of hydroxyl groups at 3400 cm$^{-1}$.

Example 2

The hydroxyl groups of macromonomer M-1B made by following the procedure of reference example 2 are esterified by adding 197.93 g (1.98 mol) succinic anhydride and 0.56 g triethylamine to 362.71 g macromonomer M-1B while stirring for four hours at 90° C. In the IR-spectrum the esterified macromonomer containing dicarboxylic half ester units shows no absorption of hydroxyl groups at 3400 cm$^{-1}$. The viscosity measured with a Bohlin rheometer is $\eta_{dyn}$=245 Pas (25° C.).

Example 3

The hydroxyl groups of macromonomer M-1F made by following the procedure of reference example 3 are esterified by adding 31.58 g (0.32 mol) succinic anhydride, 0.11 g triethylamine and 13.58 g triethyleneglycol dimethacrylate to 107.57 g of a macromonomer-triethylenglycol dimethacrylate mixture (containing 74.40 g, 0.08 mol macromonomer M-1F) while stirring for two hours at 90° C. In the IR-spectrum the esterified macromonomer containing dicarboxylic half ester units shows no absorption of hydroxyl groups at 3400 cm$^{-1}$. $\theta_{dyn}$=55.2 Pas (25° C.).

Example 4

The hydroxyl groups of macromonomer M-3 wherein each E is hydroxyl made by following the procedure of reference example 4 are esterified by adding to 40,000 g of a macromonomer-triethyleneglycol dimethacrylate mixture (containing 27,844 g, 23.32 mmol macromonomer M-3 wherein each E is a hydroxy moiety), 9,338 g (93.32 mmol) succinic anhydride and 12,156 g triethylenglycol dimethacrylate while stirring for two hours at 90° C. The IR-spectrum does not show any absorption of hydroxyl groups at 3400 cm$^{-1}$ of the newly modified macromonomer containing dicarboxylic half ester units.

Example 5

The hydroxyl groups of macromonomer M-5 wherein each E is hydroxyl made by following the procedure of reference example 5 are esterified by adding 23,516 g (235.00 mmol) succinic anhydride to a macromonomer M-5 wherein each E is hydroxyl for four hours at 90° C. In the IR-spectrum the esterified macromonomer containing dicarboxylic half ester units show no absorption of hydroxyl groups at 3400 cm$^{-1}$. The macromonomer is characterised by the following analytical data:

Melting point: Fp.=46.6° C.

Elemental analysis: ($C_{93}H_{120}N_4O_{24}$) 1678,01

|  | calc. | C 66,57 | H 7,24 | N 3,34 |
|---|---|---|---|---|
|  | found | C 66,60 | H 6,80 | N 2,73 |

Example 6

The hydroxyl groups of macromonomer M-5 wherein each E is hydroxyl made by following the procedure of reference example 5 are esterified by adding 8,239 g (42.88 mmol) trimellitic anhydride, 0.2 g N,N-bis(β-hydroxyethyl)-p-toluidin, 140 ml dioxane and 9,247 g triethylenglycol dimethacrylate to 40.008 g of a macromonomer-triethylenglycol dimethacrylate-mixture (containing 28,000 g, 21.44 mmol macromonomer M-5 wherein each E is hydroxyl) and kept for eight hours at 90° C. After evaporation of the dioxane, the macromonomer was washed with petrol ether and dried at 40° C. within six hours. In the IR-spectrum the newly modified macromonomer containing two dicarboxylic half ester units and two hydroxylic groups per average molecule show absorption of hydroxyl groups at 3400 cm$^{-1}$ and of the ester unit at 1720 cm$^{-1}$.

Example 7

The hydroxyl groups of macromonomer M-5 wherein each E is hydroxyl made by following the procedure of reference example 6 are esterified by adding 29,384 g (293.67 mmol) succinic anhydride to a macromonomer and kept for four hours at 90° C. In the IR-spectrum the esterified macromonomer M-5 wherein each E is hydrogen (n=0) containing dicarboxylic half ester units shows no absorption of hydroxyl groups at 3400 cm$^{-1}$.

Example 8

The hydroxyl groups of macromonomer M-6 wherein each E is hydroxyl made by following the procedure of reference example 7 are esterified by adding 12,966 g (0.130 mol) succinic anhydride and 0.2 g N,N-bis(β-hydroxyethyl)-p-toluidin to 50,000 g of a macromonomer-triethylenglycol dimethacrylate mixture (containing 35,000 g, 0.032 mol macromonomer M-6 wherein each E is hydroxyl) while stirring and were kept for eight hours at 50° C.

In the IR-spectrum the esterified macromonomer containing dicarboxylic half ester units shows no absorption of hydroxyl groups at 3400 cm$^{-1}$.

Example 9

The hydroxyl groups of macromonomer M-7 wherein each E is hydroxyl made by following the procedure of reference example 8 are esterified by adding 12,966 g (0.130 mol) succinic anhydride and 0.2 g N,N-bis(β-hydroxyethyl)-p-toluidin to 50,000 g of a macromonomer-triethylenglycol dimethacrylate mixture (containing 35,000 g, 0.032 mol macromonomer M-7 wherein each E is hydroxyl) while stirring and kept for two hours at 80° C. The IR-spectrum does not show any absorption of hydroxyl groups at 3400 cm$^{-1}$ of the esterified macromonomer containing dicarboxylic half ester units.

Example 10

The hydroxyl groups of macromonomer M-6 wherein each E is hydroxyl made by following the procedure of reference example 7 are esterified by adding 29,760 g (0.297 mol) succinic anhydride and 0.2 g N,N-bis(β-hydroxyethyl)-p-toluidin to a macromonomer M-6 wherein each E is hydroxyl while stirring and were kept for eight hours at 50° C. In the IR-spectrum the newly modified macromonomer containing dicarboxylic half ester units shows no absorption of hydroxyl groups at 3400 cm$^{-1}$.

Example 11

The hydroxyl groups of macromonomer M-1A made by following the procedure of reference example 1 are esterified by adding 40,000 g (40.03 mmol) of a macromonomer M-1A dissolved in 100 ml THF 16,204 g triethylamine in 50 ml THF. After adding 24,553 g POCl$_3$ (153.33 mmol) drops by drops while stirring at 0° to 5° C. the solution is stirred for further two hours at room temperature. Than the triethylamine hydrochloride is filtered off and the mixture is hydrolysed with 20 ml water. The organic solution is extracted three times with Na$_2$CO$_3$ solution and is separated from water. From the solution, dried over MgSO$_4$, the solvent is evaporated and the macromonomer is dried.

In the IR-spectrum the esterified macromonomer containing phosphoric ester units shows no absorption of hydroxyl groups at ν=3400 cm$^{-1}$. New absorptions were found at ν=1007 cm$^{-1}$, ν=2362 cm$^{-1}$ and as shoulder at ν=3302 cm$^{-1}$. In the $^1$H NMR spectrum signals of the olefinic double bonds at $\delta_{(CH2=)}$=6.06/6.12 ppm and at $\delta_{(CH2=)}$=5.58/5.59 ppm were found. The signals of the methine protons (CH—OP) appears at $\delta_{(CH)}$=5.22 and 5.88 ppm. Those of unreacted macromonomer (CH—OH) appears at $\delta_{(CH)}$=4.34/4.35 ppm.

The HPLC analysis of the modified macromonomer shows the same distribution of oligomers as those of unreacted M-1. Consequently, only the oligomer analogous reaction takes place which does not change the distribution, and no side reaction or crosslinking was observed.

Example 12

The hydroxyl groups of macromonomer with M-3 wherein each E is hydroxyl made by following the procedure of reference example 4 are esterified by adding 60,000 g (50.26 mmol) of a macromonomer M-3 wherein each E is hydroxyl dissolved in 150 ml THF to 20,346 g triethylamine in 50 ml THF. After adding 30,829 g (201.06 mmol) POCl$_3$ drops by drops while stirring at 0° to 5° C. the solution is stirred for further two hours at room temperature. Than the triethylamine hydrochloride is filtered off and the mixture is hydrolysed with 20 ml water. The organic solution is extracted three times with Na$_2$CO$_3$ solution and is separated from water. From the solution, dried over MgSO$_4$, the solvent is evaporated and the macromonomer is dried.

In the IR-spectrum the esterified macromonomer containing phosphoric ester units shows no absorption of hydroxyl groups at ν=3400 cm$^{-1}$. New absorptions are found at ν=1007 cm$^{-1}$, ν=2362 cm$^{-1}$ and as shoulder at ν=3302 cm$^{-1}$ and an broad absorption at ν=2600 to 2800 cm$^{-1}$ of the ammonium salt.

Example 13

The hydroxyl groups of macromonomer M-6 wherein each E is hydroxyl made by following the procedure of reference example 7 are esterified by adding 40,000 g (37.83 mmol) of a macromonomer M-6 wherein each E is hydroxyl dissolved in 100 ml THF to 15,312 g triethylamine in 50 ml THF. After adding 23,200 g (151.31 mmol) POCl$_3$ drops by drops while stirring at 0° to 5° C. the solution is stirred for further two hours at room temperature. Than the triethylamine hydrochloride is filtered off and the mixture is hydrolysed with 20 ml water. The organic solution is extracted three times with Na$_2$CO$_3$ solution and is separated from water. From the solution, dried over MgSO$_4$, the solvent is evaporated and the macromonomer is dried.

In the IR-spectrum the esterified macromonomer containing phosphoric ester units shows no absorption of hydroxyl groups at ν=3400 cm$^{-1}$. New absorptions are found at ν=1007 cm$^{-1}$, ν=2362 cm$^{-1}$ and as shoulder at ν=3302 cm$^{-1}$.

Example 14

1) 75% of hydroxyl groups of the macromonomer M-1A made by following procedure of reference example 1 are esterified with succinic acid anhydride by adding 148,387 g (0.116 mol) of a macromonomer M-1A to 34,890 g (0.349 mol) succinic anhydride and 0.183 g triethylamine and reacted for two hours at 80° C. while stirring. The macromonomer is dissolved in 250 ml THF and stirred for a further hour. The esterified macromonomer M-1A containing (n+2)-carboxylic half ester groups show in the IR-spectrum an absorption of ν$_{CO}$=1720 cm$^{-1}$.

2) Esterification of the residual unreacted hydroxyl groups of the macromonomer with POCl$_3$.

To 183,460 g (0.141 mol) of the obtained macromonomer M-1A dissolved in 250 ml THF were added 14,287 g triethylamine in 50 ml THF. After adding 21,659 g (0.141 mol) POCl$_3$ drops by drops while stirring at 0° to 5° C. the solution is stirred for further two hours at room temperature. Than the triethylamine hydrochloride is filtered off and the mixture is hydrolysed with 50 ml water. The organic solution is extracted three times with Na$_2$CO$_3$ solution and is separated from water. From the solution, dried over MgSO$_4$, the solvent is evaporated and the macromonomer is dried. In the IR-spectrum the esterified macromonomer containing phosphoric ester units shows no absorption of hydroxyl groups at ν=3400 cm$^{-1}$. New absorptions are found at ν=1007 cm$^{-1}$, ν=2362 cm$^{-1}$ and as shoulder at ν=3302 cm$^{-1}$. In the $^1$H NMR spectrum signals of the olefinic double bonds at δ$_{(CH2=)}$=6.06/6.12 ppm and at δ$_{(CH2=)}$=5.58/5.59 ppm were found. The signals of the methine protons (CH—O—P) appear at δ$_{(CH)}$=5.22 and 5.88 ppm. Those containing succinic half ester units appear at δ$_{(CH)}$=5.38 ppm. The esterified macromonomer M-1 containing (n+2)-carboxylic half ester groups and n-phosphoric acid groups is described by the following formula (n=1, R=—OC$_6$H$_4$—C(CH$_3$)$_2$—C$_6$H$_4$O—, R$_2$=—(CH$_2$)$_4$—, R$_5$=—CH$_2$CH$_2$—):

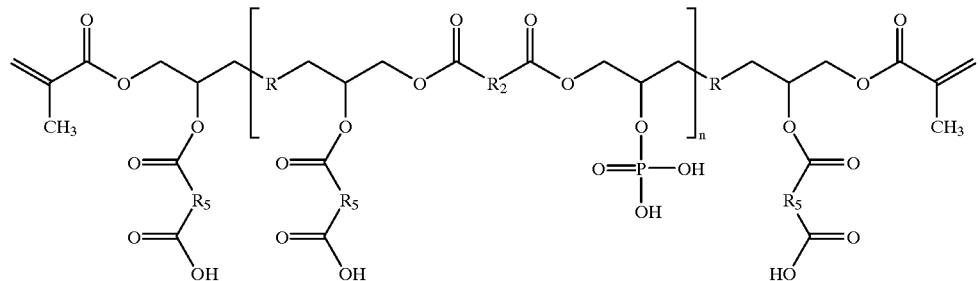

Example 15

100.00 g (161.29 mmol) of a monophosphate ester of pentaerythrit pentmethacrylate and 27.29 g (161.29 mmol) dimethylaminoethyl methacylate are dissolved in 84.86 g triethyleneglycol dimethacrylate and reacted for two hours at 50° C. In the IR spectrum at 2600 to 2850 cm$^{-1}$ an absorption of the ammonium salt is found.

At 3400 cm$^{-1}$ no absorption of OH-groups is observed. The pH of the salt is 3,9.

Application Example 1

(Dental Adhesive)

1,242 g of the esterified macromonomer M-5 wherein each E is succinic acid half ester made by following the procedure of example 5, 0.411 g triethyleneglycol dimethacrylate, 0.008 g N,N-bis(β-hydroxyethyl)-p-toluidine and 0.006 g camphorquinone were homogeneously mixed. This mixture was applied in a ring (2 mm high, 5 mm i.d.) on the surface of teeth and exposed with visible light (irradiation lamp Prismetics Lite De Trey Dentsply) for 40 seconds. Immediately after fixation, the teeth are transferred for 24 hours to a chamber at 37±2° C. and 100% relative humidity. The adhesion measured with a Zwick-apparatus is 3.74±1.29 MPa.

Comparative Example 1

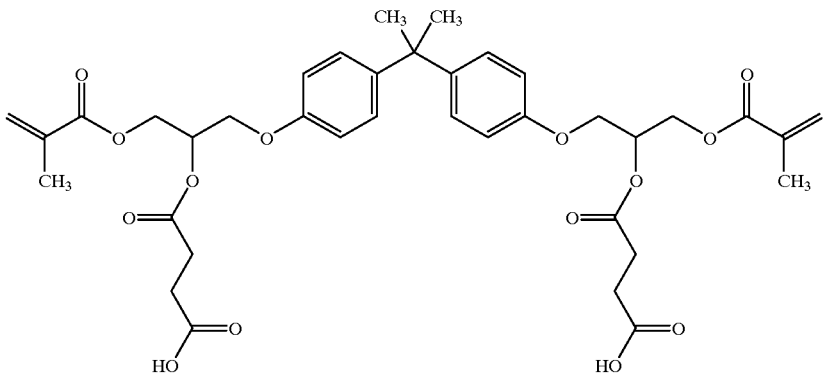

2,420 g of 2,2-Bis-[p-(2-hydroxy-3-methacryloyloxypropoxy)-phenyl]-propan (Bis-GMA) which is modified with succinic anhydride at the hydroxyl groups, 0.821 g triethylenglycol dimethacrylate, 0.016 g N,N-bis(β-hydroxyethyl)-p-toluidine and 0.012 g camphorquinone were homogeneously mixed. This mixture is applied in a ring (2 mm high, 5 mm i.d.) on the surface of teeth and exposed with visible light (irradiation lamp Prismetics Lite De Trey Dentsply) for 40 seconds. Immediately after fixation, the teeth are transferred for 24 hours to a chamber at 37±2° C. and 100% relative humidity. The adhesion is 0.45±20 Mpa, when measured with a Zwick-apparatus model number 1455, manufactured by Zwick GmbH & Co.

Application Example 2
(Dental Adhesive)

1,276 g of the esterified macromonomer M-5 wherein each E is succinic acid half ester made by following the procedure of example 5, 2,126 g triethylenglycol dimethacry-late, 6.5 g Strontium-alumo-silicate glass, 0.036 g camphorquinone and 0.045 g N,N-bis(β-hydroxyethyl)-p-toluidine are homogeneously mixed and polymerized photochemical. The product has the following properties: adhesin to dentine of 3.7±1.1 MPa, compressive strength 177±3.5 MPa, Elastic Modulus of 2383±71 MPa.

Application Example 3
(Dental Adhesive)

1,755 g of macromonomer M-5 wherein each E is succinic acid half ester of example 5, 0.752 g methylmethacrylate, 4,652 g Strontium-alumo-silicate glass, 0.010 g camphorquinone and 0.012 g N,N-bis(β-hydroxyethyl)-p-toluidine are homogeneously mixed and polymerized photochemically. The product obtained has the following properties: adhesion to dentine: 3.9±1.2 MPa, compressive strength 134±9.7 MPa, Elastic Modulus 2528±158 MPa.

Application Example 4
(Dental Adhesive)
Paste A 3.0404 g of macromonomer M-5 wherein each E is succinic acid half ester of example 5, 2.2512 g triethylenglycol dimethacrylate, 6.0 g $CaWO_4/ZrO_2$ (80/20) and 0.3135 g Strontium-alumo-silicate glass containing 10% lithium-sulfinate are homogeneously mixed.
Paste B 3.0404 g of macromonomer M-5 wherein each E is succinic acid half ester of example 5, 2.2512 g triethylenglycol dimethacrylate, 6.0 g $CaWO_4/ZrO_2$ (80/20), 0.0057 g octophen and 0.0668 g Strontium-alumo-silicate glass containing 1% Cu-(I)-thiourea complex are homogeneously mixed.

Immediately before use paste A and paste B were mixed in the wt.-ratio 1:1 homogeneously. The gel time at 23° C. is estimated to be 32 min. and the gel time at 23° C. is 7 minutes. The radio-opacity (RO) of the obtained material is 6.5 mm/mm Al.

Application Example 5
(Dental Adhesive)
Paste A 8,001 g of macromonomer M-1A of example 1, 5,334 g triethylenglycol dimethacrylate, 14,467 g $CaWO_4/ZrO_2$ (80/20), 0.014 g 2.6-di-tert.-butyl-p-cresol and 0.533 g Strontium-alumo-silicate glass containing 10% lithium-sulfinate are homogeneously mixed.
Paste B 8,001 g of macromonomer M-1A of example 1, 5,334 g triethylenglycol dimethacrylate, 14,467 g $CaWO_4/ZrO_2$ (80/20), 0.014 g 2,6-di-tert.-butyl-p-cresol, 0.065 g octophen and 0.0533 g Strontium-alumo-silicate glass containing 1% Cu-(I)-thiourea complex are homogeneously mixed.

Immediately before use paste A and paste B were mixed in the wt.-ratio 1:1 homogeneously. The gel time at 23° C. is about 96 minutes, and the gel time at 32° C. is 19 min. The radioopacity of the obtained material is about about 6.7 mm/mm Al.

Application Example 6
(Dental Adhesive)
Powder 15,000 g silylated Strontium-alumo-silicate glass and 2,000 g silylated Strontium-alumo-silicate glass containing 10% dibenzoylperoxide were mixed homogeneously.
Liquid 14,000 g of a macromonomer M-5 wherein each E is succinic acid half ester of example 5, 6,000 g tetrahydrofurfuryl-methacrylate, 0.405 g N,N-bis(β-hydroxyethyl)-p-toluidine, 0.0130 g 2,6-di-tert.-butyl-p-cresol are mixed homogeneously.

Immediately before use powder and liquid were mixed in the wt.-ratio 1.73:1.00 homogeneously. The working time is 3.50 minutes and the setting time is 3.25 minutes. The adhesion to dentine is measured to be 2.2±0.7 MPa. The composite shows the following mechanical properties: compressive strength: 152±15 MPa, and elastic modulus of 1788±81 MPa.

Application Example 7
(Dental Adhesive)
Paste A 3,000 g of an ammonium salt of dipenta erthrytrol pentamethacrylate monophosphate and 2-(dimetyl)aminoethyl methacrylate (AP-1), 2,000 g macromonomer M-1A of example 1, 5,000 g triethylenglycol dimethacrylate, 15,000 g Strontium-alumo-silicate glass, 0.005 g 2,6-di-tert.-butyl-p-cresol and 0.200 g cumenhydroperoxide are mixed homogeneously.

Paste B 3,000 g of AP-1, 2,000 g macromonomer M-1A of example 1, 5,000 g triethylenglycol dimethacrylate, 15,000 g Strontium-alumo-silicate glass, 0.005 g 2,6-di-tert.-butyl-p-cresol, 0.4081 g of a 0,1% solution of cupric acetylacetonate in 2-hydroxy propylmethacrylate and 0.041 g ascorbic acid palmitate are mixed homogeneously.

The following values are measured: gel time (gt) at 23° C. is 3:55 minutes, gel time is 37° C. is 2.10 minutes, adhesion to dentine 5.12 MPa, shrinkage (reduction in volume) is 4.33%.

Application Example 8
(Dental Adhesive)
Paste A 3,000 g of AP-1, 2,000 g of macromonomer M-1A of example 1, 5,000 g triethylenglycol dimethacrylate, 15,000 g Strontium-alumo-silicate glass, 0.005 g 2,6-di-tert.-butyl-p-cresol and 0.200 g tert.-butyl peroxy benzoate are mixed homogeneously.

Paste B 3,000 g of AP-1, 2,000 g macromonomer M-1A of example 1, 5,000 g triethylenglycol dimethacrylate, 15,000 g Strontium-alumo-silicate glass, 0.005 g 2,6-di-tert.-butyl-p-cresol, 0.6186 g of a 0,1% solution of cupric acetyacetonate in 2-hydroxy-propylmethacrylate and 0.051 g ascorbic acid palmitate are mixed homogeneously.

The following values were measured: gel time (gt) at 23° C. is 6.10 minutes, (gt) at 37° C. is 3.20 minutes, adhesion to dentine 4.02 MPa, shrinkage (or reduction in volume) is 4.33%.

Application Example 9
(Dental Adhesive)
Powder 41.842 g silylated Strontium-alumo-silicate glass and 0.423 g dibenzoyl peroxide are mixed homogeneously.

Liquid 18,000 g of AP-1, 12,000 g triethylenglycoldimethacrylate, 0.180 g N,N-dimethyl-3,5-dimethyl aniline and 0.009 g 2,6-di-tert.-butyl-p-cresol were mixed homogeneously. Immediately before use powder and liquid were mixed in the weight ratio 1.40:1.00 homogeneously. The working time is 1:30 minutes and the setting time is 2:30 minutes.

The following properties are measured:
adhesion to dentine: 7.68±1.5 MPa
compressive strength: 261±14 MPa
Elastic modules: 2917±76 MPa
shrinkage: 2.30% (percent reduction in volume)
expansion: 1.17% (after storage for 14 weeks in water at 37° C.) (expansion in length)
fluoride release: 5.33 µg/cm$^2$ (after storage for 9 weeks in water at 37° C.).

Application Example 10
(Dental Adhesive)
Powder 47.0 g silylated Strontium-alumo-silicate glass, 07544 g dibenzoyl peroxide and 2.52 g SrF$_2$ are mixed homogeneously.

Liquid 28,570 g of an ammonium salt of dipentaerthrytrolpentamethacrylate monophosphate and 2-(dimetyl)aminoethyl methacrylate (AP-1) containing 8,570 g triethylenglycol dimethacrylate, 7,140 g macromonomer M-1A of example 1 containing 2,140 g triethylenglycol dimethacrylate, 13,990 g triethylenglycol dimethacrylate 0.250 g N,N-bis(β-hydroxyethyl)-p-toluidine and 0.05 g 2,6-di-tert.-butyl-p-cresol are mixed homogeneously.

Immediately before use powder and liquid are mixed in the weight ratio 1.40:1.00 homogeneously. The working time is 5:50 minutes and the setting time is 4:15 minutes.

The following properties are measured:
adhesion to dentine: 7.7±0.8 MPa
compressive strength: 295±9 g MPa (ISO 9917, EN 29917)
flexural strength: 77.1±7.1 MPa (ISO 4049, EN 24049)
Elastic modulus: 4482±147 MPa (ISO 4049, EN 24049)
Opacity: 90.6% (ISO 9912, EN 29912)
shrinkage ΔV: 5.8±0.5%
expansion ΔL: 1.52% (after storage for 28 weeks in water at 37° C.)
fluoride release: 64.01 µg/cm$^2$ (after storage for 27 weeks in water at 37° C.).

Application Example 11
(Dental Adhesive)
Powder 46,2480 g silylated Strontium-alumo-silicate glass, 0.6937 g dibenzoyl peroxide and 2.3124 g SrF$_2$ are mixed homogeneously.

Liquid 20,0000 g of AP-1 containing 14,0000 g triethylenglycol dimethacrylate, 5,0000 g macromonomer M-1A of example 1 containing 1.5000 g triethylenglycol dimethacrylate, 1.323 g demineralised water, 4,0000 g UDMA, 4.7000 g triethylenglycol dimethacrylate, 0.1485 g N,N-bis(β-hydroxyethyl)-p-toluidine and 0.0098 g 2,6-di-tert.-butyl-p-cresol are mixed homogeneously. The viscosity measured with a Bohlin rheometer is $\theta_{dyn}$=1.086±0.005 Pas (23° C.).

Immediately before use powder and liquid are mixed in the weight ratio 1.40:1.00 homogeneously. The working time is 4:00 minutes and the setting time is 4:00 minutes.

The following properties were measured:
adhesion to dentine: 5.86±1.53 MPa
compressive strength: 301±11 MPa
flexural strength: 74.8±4.8 MPa
Elastic modulus: 5320±271 MPa
expansion ΔL: 1.10% (after storage for 5 weeks in water at 37° C.)
fluoride release: 114.05 µg/cm$^2$ (after storage for 28 weeks in water at 37° C.).

Application Example 12
(Dental Sealant)

20.00 g macromonomer M-1A of example 1, 19.63 g triethylenglycol dimethacrylate, 0.18 g N,N-bis(β-hydroxyethyl)-p-toluidine, 0.12 g camphorquinone, 0.07 g 2,6-di-tert.-butyl-p-cresol and 60.00 g Strontium-alumo-silicate glass are mixed homogeneously. Results are given in table 1.

Application Example 13
(Dental Sealant)

20.00 g macromonomer M-1A of example 14, 19.63 g triethylenglycol dimethacrylate, 0.18 g N,N-bis(β-hydroxyethyl)-p-toluidine, 0.12 g camphoro quinone, 0.07 g 2,6-di-tert.-butyl-p-cresol and 60.00 g Strontium-alumo-silicate glass are mixed homogeneously. Results are given in table 1.

Comparative Example 2

20.00 g of 2,2-Bis-[p-(2-hydroxy-3-methacryloyloxypropoxy)-phenyl]-propan (Bis-GMA) which is modified with succinic anhydride at the hydroxyl groups, 19.63 g triethylenglycol dimethacrylate, 0.18 g N,N-bis(β-hydroxyethyl)-p-toluidine, 0.12 g camphorquinone, 0.07 g 2,6-di-tert.-butyl-p-cresol and 60.00 g Strontium-alumo-silicate glass are mixed homogeneously. Results are given in table 1.

TABLE 1

|  | Macromonomer M-1A according example 12 | Macromonomer M-1A according example 13 | Bis-GMA according comparative example 2 |
|---|---|---|---|
| Adhesion to dentin MPa | 2.35 | 2.42 | 1.04 |
| Standard deviation MPa | ±0.79 | ±1.06 | ±0.34 |
| Molecular weight of modified Macromonomer | 1399.4 | 1379.3 | 712.3 |
| Molecular weight per ester unit | 349.9 | 344.8 | 356.2 |

Application Example 14

(Dental Sealant)

10.00 g of AP-1 containing 3.00 g triethylenglycol dimethacrylate, 2.50 g macromonomer M-1A of example 1 containing 0.75 g triethylenglycol dimethacrylate, 1.25 g triethylenglycol dimethacrylate, 0.0875 g N,N-bis(β-hydroxyethyl)-p-toluidine, 0.0875 g camphor quinone, 11.49 g Strontium-alumo-silicate glass, 0.30 g Aerosil and 0.0088 g 2,6-di-tert.-butyl-p-cresol are mixed homogeneously. The viscosity measured with a Bohlin rheometer is $\theta_{dyn}=1.086\pm0.005$ Pas (23° C.).

Application Example 15

(Dental/medical Composite)

2,000 g macromonomer M-6 of example 8 containing 0.400 g triethylenglycol dimethacrylate, 5,273 g Strontium-alumo-silicate glass, 0.010 g champhorquinon and 0.012 g N,N-bis(β-hydroxyethyl)-p-toluidin are homogeneously mixed and polymerized photochemical. The composite shows the following mechanical properties:

flexural strength: 76.6±4.5 MPa
flexural modules: 5074.0±321 MPa
compressive strength: 215.0±6.0 MPa
Elastic modules: 3180.0±88 Mpa It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A dental composition comprising:

from about 5 to about 20 percent by weight of an esterified macromonomer within the scope of formula:

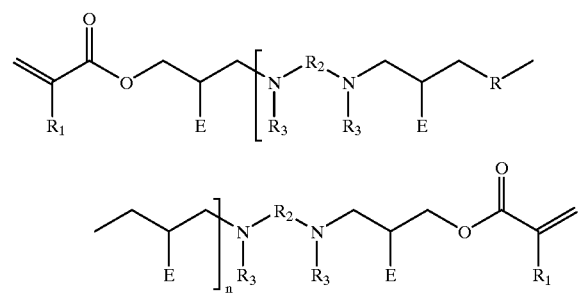

M-5 wherein
each E independently is an organic or inorganic ester moiety and at least one E is an organic ester moiety or inorganic ester moiety,
R is a diether containing moiety, or diester containing moiety or tertiary amine containing moiety,
$R_1$ is hydrogen or an alkyl having from 1 to 12 carbon atoms, oxyalkyl having from 1 to 12 carbon atoms, alkenyl having from 2 to 12 carbon atoms, cycloalkyl having from 5 to 12 carbon atoms, aryl having from 6 to 12 carbon atoms or aralkyl having from 7 to 12 carbon atoms,
$R_2$ is a difunctional alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms,
$R_3$ is an alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms,
and n is an integer of at least 1,
from about 10 to about 25 percent by weight of a di- or poly(meth)acrylate monomer having at least one phosphorous acid ester group,
from about 20 to about 35 percent by weight of a polymerizable monomer,
from about 50 to about 65 percent by weight of a filler and polymerization initiator and stabilizers.

2. A dental composition, comprising:

from about 5 to about 25 percent by weight of an esterified macromonomer within the scope of formula:

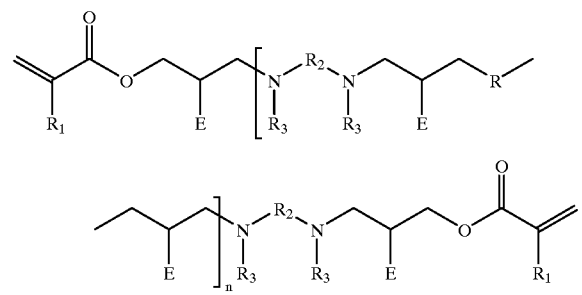

M-5 wherein
each E independently is an organic or inorganic ester moiety,

R is a diether containing moiety, or diester containing moiety or tertiary amine containing moiety, $R_1$ is hydrogen or an alkyl having from 1 to 12 carbon atoms, oxyalkyl having from 1 to 12 carbon atoms, alkenyl having from 2 to 12 carbon atoms, cycloalkyl having from 5 to 12 carbon atoms, aryl having from 6 to 12 carbon atoms or aralkyl having from 7 to 12 carbon atoms, $R_2$ is a difunctional alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms, $R_3$ is an alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms, and n is an integer of at least 1, from about 5 to about 25 percent by weight of di- or poly(meth)acrylate monomer having at least one phosphorous acid ester group, from about 7 to about 40 percent by weight of a polymerizable monomer, from about 50 to about 85 percent by weight of a fluoride releasing inorganic filler and polymerization initiator and stabilizers, said composition being adapted to form polymeric material having an exposed surface and a fluoride release of at least 1 g F- per week at 37° C. per cm2 of said exposed surface.

3. A dental composition comprising:

from about 5 to about 25 percent by weight of an esterified macromonomer within the scope of formula:

M-5

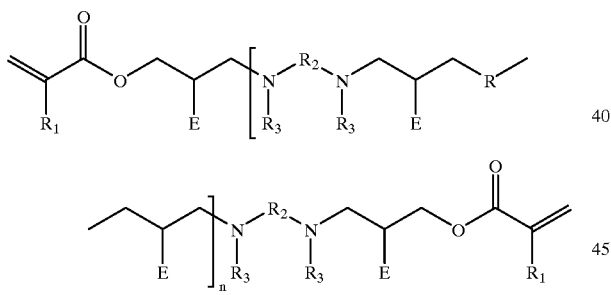

wherein each E independently is an organic or inorganic ester moiety and at least one E is an organic ester moiety or inorganic ester moiety, R is a diether containing moiety, or diester containing moiety or tertiary amine containing moiety, $R_1$ is hydrogen or an alkyl having from 1 to 12 carbon atoms, oxyalkyl having from 1 to 12 carbon atoms, alkenyl having from 2 to 12 carbon atoms, cycloalkyl having from 5 to 12 carbon atoms, aryl having from 6 to 12 carbon atoms or aralkyl having from 7 to 12 carbon atoms, $R_2$ is a difunctional alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms, $R_3$ is a alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms, and n is an integer of at least 1, from about 10 to about 30 percent by weight of di- or poly(meth)acrylate monomer having at least one phosphorous acid ester group, from about 20 to about 40 percent by weight of a polymerizable monomer, from about 10 to about 50 percent by weight of a filler and polymerization initiator and stabilizers.

4. A dental composition comprising:

from about 5 to about 25 percent by weight of an esterified macromonomer within the scope of formula:

M-5

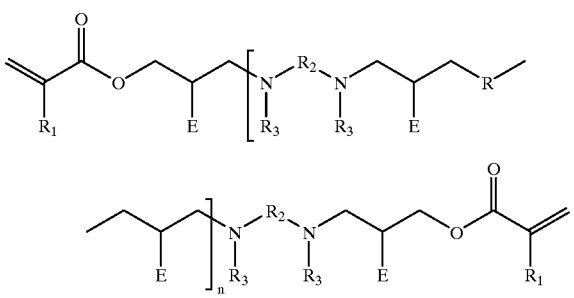

wherein each E independently is an organic or inorganic ester moiety and at least one E is an organic ester moiety or inorganic ester moiety, R is a diether containing moiety, or diester containing moiety or tertiary amine containing moiety, $R_1$ is hydrogen or an alkyl having from 1 to 12 carbon atoms, oxyalkyl having from 1 to 12 carbon atoms, alkenyl having from 2 to 12 carbon atoms, cycloalkyl having from 5 to 12 carbon atoms, aryl having from 6 to 12 carbon atoms or aralkyl having from 7 to 12 carbon atoms, $R_2$ is a difunctional alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms, $R_3$ is an alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms, and n is an integer of at least 1, from about 5 to about 30 percent by weight of di- or poly(meth)acrylate monomer having at least one phosphorous acid ester group, from about 10 to about 40 percent by weight of a polymerizable monomer, from about 30 to about 90 percent by weight of a diluent and polymerization initiator and stabilizers.

5. A dental composition comprising:

from about 1 to about 25 percent by weight of an esterified macromonomer, di- or poly(meth) acrylate monomer having at least one phosphous acid ester group and a polymerizable monomer and polymerization initiator from about 75 to about 99 percent by weight of an organic solvent and polymerization co-initiator said esterified macromonomer being within the scope of formula:

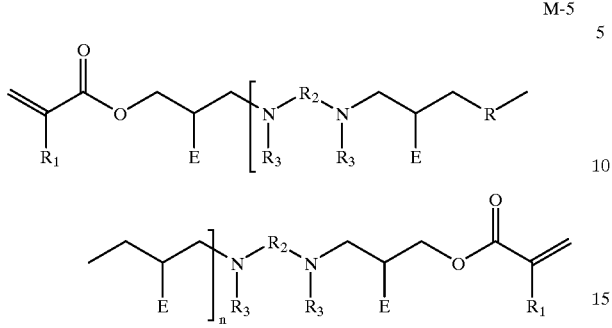

M-5 wherein
each E independently is an organic or inorganic ester moiety and at least one E is an organic ester moiety or inorganic ester moiety,
R is a diether containing moiety, or diester containing moiety or tertiary amine containing moiety,
$R_1$ is hydrogen or an alkyl having from 1 to 12 carbon atoms, oxyalkyl having from 1 to 12 carbon atoms, alkenyl having from 2 to 12 carbon atoms, cycloalkyl having from 5 to 12 carbon atoms, aryl having from 6 to 12 carbon atoms or aralkyl having from 7 to 12 carbon atoms,
$R_2$ is a difunctional alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms,
$R_3$ is an alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms,
and n is an integer of at least 1.

6. A dental composition comprising:
from about 5 to about 20 percent by weight of an esterified macromonomer within the scope of formula M-5:

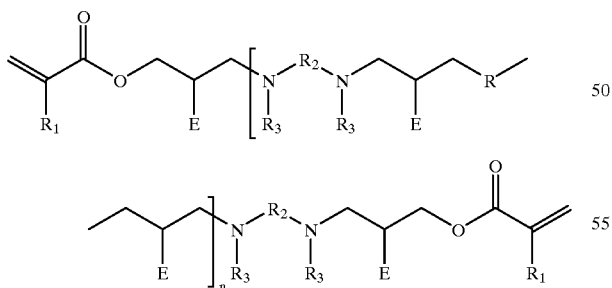

M-5 wherein
each E independently is an organic or inorganic ester moiety and at least one E is an organic ester moiety or inorganic ester moiety,
R is a diether containing moiety, or diester containing moiety or tertiary amine containing moiety,
$R_1$ is hydrogen or an alkyl having from 1 to 12 carbon atoms, oxyalkyl having from 1 to 12 carbon atoms, alkenyl having from 2 to 12 carbon atoms, cycloalkyl having from 5 to 12 carbon atoms, aryl having from 6 to 12 carbon atoms or aralkyl having from 7 to 12 carbon atoms,
$R_2$ is a difunctional alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms,
$R_3$ is an alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms,
and n is an integer of at least 1,
from about 10 to about 25 percent by weight of a di- or poly(meth)acrylate monomer having at least one phosphorous acid ester group,
from about 20 to about 35 percent by weight of a polymerizable monomer,
from about 50 to about 65 percent by weight of a filler and polymerization initiator and stabilizers.

7. The polymeric product formed from the polymerization of the composition of claim 6 having an adhesion to dentine of at least 2 MPa, a fluoride release of at least 1 µg F⁻ per week and per cm² of the exposed surface of the composition, an opacity of at least $C_{0.7}=40\%$ and a compressive strength of at least 200 MPa.

8. A dental composition comprising:
from about 5 to about 25 percent by weight of an esterified macromonomer,
from about 10 to about 30 percent by weight of di- or poly(meth)acrylate monomer having at least one phosphorous acid ester group,
from about 20 to about 40 percent by weight of a polymerizable monomer,
from about 10 to about 50 percent by weight of a filler and polymerization initiator and stabilizers said esterified macromonomer being within the scope of formula M-5:

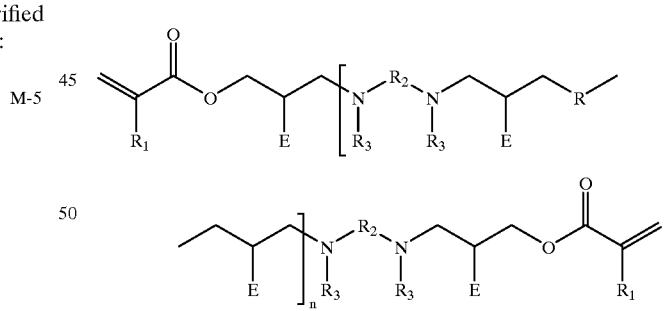

M-5 wherein
each E independently is an organic or inorganic ester moiety and at least one E is an ester moiety or inorganic ester moiety,
R is a diether containing moiety, or diester containing moiety or tertiary amine containing moiety,
$R_1$ is hydrogen or an alkyl having from 1 to 12 carbon atoms, oxyalkyl having from 1 to 12 carbon atoms, alkenyl having from 2 to 12 carbon atoms, cycloalkyl having from 5 to 12 carbon atoms, aryl having from 6 to 12 carbon atoms or aralkyl having from 7 to 12 carbon atoms, $R_2$ is a difunctional alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms, $R_3$ is an alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms, and n is an integer of at least 1.

9. A dental composition comprising:

from about 5 to about 25 percent by weight of an esterified macromonomer, from about 5 to about 30 percent by weight of di- or poly(meth)acrylate monomer having at least one phosphorous acid ester group, from about 10 to about 40 percent by weight of a polymerizable monomer, from about 30 to about 90 percent by weight of a diluent and polymerization initiator and stabilizers, said esterified macromonomer being within the scope of formula M-5:

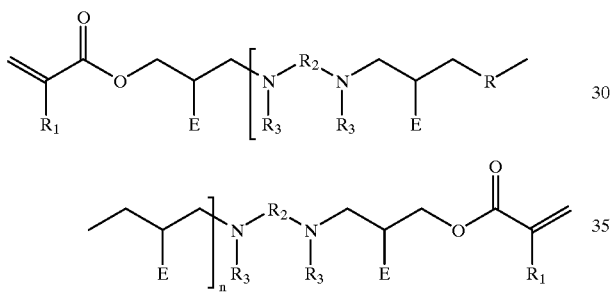

M-5 wherein each E independently is an organic or inorganic ester moiety and at least one E is an organic ester moiety or inorganic ester moiety, R is a diether containing moiety, or diester containing moiety or tertiary amine containing moiety, $R_1$ is hydrogen or an alkyl having from 1 to 12 carbon atoms, oxyalkyl having from 1 to 12 carbon atoms, alkenyl having from 2 to 12 carbon atoms, cycloalkyl having from 5 to 12 carbon atoms, aryl having from 6 to 12 carbon atoms or aralkyl having from 7 to 12 carbon atoms, $R_2$ is a difunctional alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms, $R_3$ is an alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms, and n is an integer of at least 1.

10. A dental composition comprising:

from about 1 to about 25 percent by weight of an esterified macromonomer, a di- or poly(meth) acrylate monomer having at least one phosphous acid ester group, a polymerizable monomer, a polymerization initiator and polymerization co-initiator, said esterified macromonomer being within the scope of formula M-5:

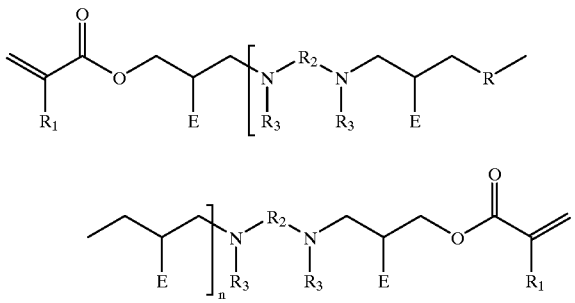

M-5 wherein each E independently is an organic or inorganic ester moiety,

R is a diether containing moiety, or diester containing moiety or tertiary amine containing moiety, $R_1$ is hydrogen or an alkyl having from 1 to 12 carbon atoms, oxyalkyl having from 1 to 12 carbon atoms, alkenyl having from 2 to 12 carbon atoms, cycloalkyl having from 5 to 12 carbon atoms, aryl having from 6 to 12 carbon atoms or aralkyl having from 7 to 12 carbon atoms, $R_2$ is a difunctional alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms, $R_3$ is an alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms, and n is an integer of at least 1.

11. A dental composition comprising:

from about 3 to about 15 percent by weight of an esterified macromonomer, from about 5 to about 25 percent by weight of di- or poly(meth)acrylate monomer having at least one phosphorous acid ester group, from about 7 to about 40 percent by weight of a polymerizable monomer, from about 50 to about 85 percent by weight of a filler and polymerization initiator and stabilizers said esterified macromonomer being within the scope of formula M-5:

M-5

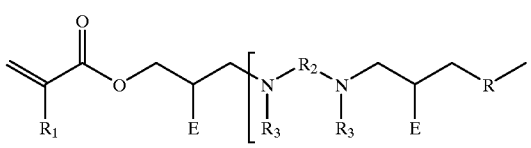

-continued

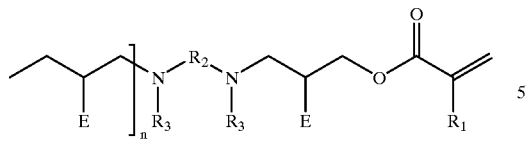

wherein
each E independently is an organic or inorganic ester moiety and at least one E is an organic ester moiety or inorganic ester moiety,
R is a diether containing moiety, or diester containing moiety or tertiary amine containing moiety,
$R_1$ is hydrogen or an alkyl having from 1 to 12 carbon atoms, oxyalkyl having from 1 to 12 carbon atoms, alkenyl having from 2 to 12 carbon atoms, cycloalkyl having from 5 to 12 carbon atoms, aryl having from 6 to 12 carbon atoms or aralkyl having from 7 to 12 carbon atoms,
$R_2$ is a difunctional alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms,
$R_3$ is an alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms,
and n is an integer of at least 1.

12. A dental composition comprising:
from about 5 to about 20 percent by weight of an esterified macromonomer within the scope of formula:

M-5

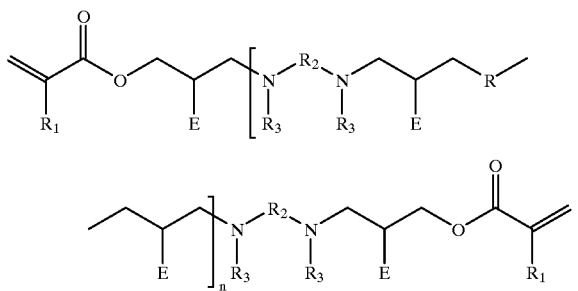

wherein
each E independently is a hydroxyl group or an organic or inorganic ester moiety obtained by esterification of a hydroxyl group with an inorganic or organic acid or a derivative thereof, which introduces pendant groups exhibiting at least one acid moiety from the group consisting of —COOH, —PO$_3$H$_2$, —SO$_3$H, BO$_2$H and salts thereof, whereby at least one E is an organic ester moiety or inorganic ester moiety, R is a diether containing moiety, or diester containing moiety or tertiary amine containing moiety,
$R_1$ is hydrogen or an alkyl having from 1 to 12 carbon atoms, oxyalkyl having from 1 to 12 carbon atoms, alkenyl having from 2 to 12 carbon atoms, cycloalkyl having from 5 to 12 carbon atoms, aryl having from 6 to 12 carbon atoms or aralkyl having from 7 to 12 carbon atoms,
$R_2$ is a difunctional alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms,
$R_3$ is an alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms,
and n is an integer from 2 to 12,
from about 10 to about 25 percent by weight of a di- or poly(meth)acrylate monomer having at least one phosphorous acid ester group,
from about 20 to about 35 percent by weight of a polymerizable monomer,
from about 50 to about 65 percent by weight of filler and polymerization initiator and stabilizers.

13. The composition of claim 12 wherein said composition is adapted to form polymeric material having an exposed surface and a fluoride release of at least 1 μg F⁻ per week at 37° C. per cm² of said exposed surface.

14. The composition of claim 12 wherein at least one E comprises a carboxyl group.

15. The composition of claim 12 wherein E is derived from succinic acid anhydride, maleic acid anhydride, dichloro maleic acid anhydride, dimethyl maleic acid anhydride, malonic acid anhydride, aconit acid anhydride, adipic acid anhydride, 3,3-tetramethylen glutaric acid anhydride, cyclohexen-1,2 acid anhydride, nadinic acid anhydride, phthalic acid anhydride, trimellitic acid anhydride, 2-sulfo-benzoic acid anhydride, 2-sulfo succinic acid anhydride, phthalic acid anhydride p-(O-phosphate), phthaloylchloride, succinic acid dimethyl ester, phosphorous penta chloride, phosphorous trichloride, phosphorous oxychloride, sulfuryl chloride, thionyl chloride, phosphor thionyl chloride, boric acid anhydride or boron trichloride.

16. The composition of claim 12 wherein said esterification is carried out in a solvent selected from the group consisting of THF, triethylenglycol bismethacrylate, diethylenglycol bismethacrylate, dioxolan bismethacrylate, spiroorthoester, spiroorthocarbonate or bicyloorthoester and 2,2-Bis[p-(acryloxyethoxy)phenyl]propane.

17. The composition of claim 12 further comprising a polymerizable monomer selected from the group consisting of mono- and polyfunctional (meth)acrylate, a urethane di- and poly(meth) acrylate, a spiro-orthoester, a spiroorthocarbonate or a bicyloorthoester.

18. The composition of claim 17 wherein polymer obtained by polymerizing said monomers has an adhesive strength to dentine of at least 2 MPa.

19. The composition of claim 12 wherein said polymerization initiator is a thermal initiator, a redox-initiator or a photoinitiator.

20. A dental composition comprising:
from about 5 to about 20 percent by weight of an esterified macromonomer within the scope of formula:

M-5

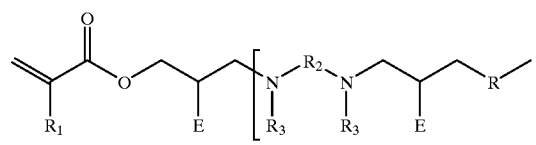

-continued

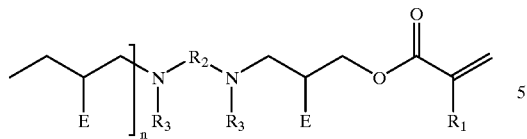

wherein
each E independently is an organic or inorganic ester moiety,
R is a diether containing moiety, or diester containing moiety or tertiary amine containing moiety,
$R_1$ is hydrogen or an alkyl having from 1 to 12 carbon atoms, oxyalkyl having from 1 to 12 carbon atoms, alkenyl having from 2 to 12 carbon atoms, cycloalkyl having from 5 to 12 carbon atoms, aryl having from 6 to 12 carbon atoms or aralkyl having from 7 to 12 carbon atoms,
$R_2$ is a difunctional alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms,
$R_3$ is an alkyl group having from 1 to 12 carbon atoms, alkenyl group having from 2 to 12 carbon atoms, cycloalkyl having from 5 to 12 carbon atoms, aryl having from 6 to 12 carbon atoms or aralkyl having from 7 to 12 carbon atoms,
and n is an integer of at least 1,
from about 10 to about 25 percent by weight of a di- or poly(meth)acrylate monomer having at least one phosphorous acid ester group,
from about 20 to about 35 percent by weight of a polymerizable monomer, from about 50 to about 65 percent by weight of a filler and polymerization initiator and stabilizers, said composition being adapted to form polymeric material having an exposed surface and a fluoride release of at least 1 $\mu$g $F^-$ per week at 37° C. per $cm^2$ of said exposed surface.

* * * * *